US007601683B2

(12) United States Patent
Chang

(10) Patent No.: US 7,601,683 B2
(45) Date of Patent: Oct. 13, 2009

(54) PROTEIN CONFORMATIONAL ISOMERS, METHODS OF MAKING, METHODS FOR USING, COMPOSITIONS COMPRISING AND PRODUCTS MADE THEREWITH

(75) Inventor: Rowen J. Y. Chang, Houston, TX (US)

(73) Assignee: Board of Regents of the University of Texas System, Houston, TX (US)

( * ) Notice: Subject to any disclaimer, the term of this patent is extended or adjusted under 35 U.S.C. 154(b) by 77 days.

(21) Appl. No.: 10/210,862

(22) Filed: Aug. 1, 2002

(65) Prior Publication Data

US 2004/0023846 A1 Feb. 5, 2004

Related U.S. Application Data

(60) Provisional application No. 60/309,543, filed on Aug. 1, 2001.

(51) Int. Cl.
*A61K 38/00* (2006.01)

(52) U.S. Cl. .......................................................... 514/2

(58) Field of Classification Search ................. 530/344, 530/350

See application file for complete search history.

(56) References Cited

U.S. PATENT DOCUMENTS

| | | | |
|---|---|---|---|
| 6,214,366 B1 | 4/2001 | Prusiner et al. |
| 6,214,565 B1 | 4/2001 | Prusiner et al. |
| 6,322,802 B1 | 11/2001 | Prusiner et al. |
| 6,900,036 B2 | 5/2005 | Chang et al. |
| 2006/0018918 A1 | 1/2006 | Chang |

FOREIGN PATENT DOCUMENTS

| | | |
|---|---|---|
| EP | 0588139 | 1/1998 |

OTHER PUBLICATIONS

Chang, J-Y. Denatured States of Tick Anticoagulant Peptide. Jan. 1, 1999. The Journal of Biological Chemistry. 274, 1, 123- 128.*

Chang, J-Y et al. Unfolding and Refolding of Cardiotoxin III Elucidated by Reversible Conversion of the Native and Scambled Species. 1998. Biochemistry. 37, 6745-6751.*

Chang, J-Y et al. The Disulfide Folding Pathway of Potato Carboxypeptidase Inibitor. Sep. 2, 1994. The Journal of Biological Chemistry. 269, 35, 22087-22094.*

Milner et al. Mutations in the B-domain of insulin-like growth factor-I influence the oxidative folding to yield products with modified biological properties. Biochemical Journal. 1995. vol. 308, pp. 865-871.*

Clarke et al. Engineered Disulfide Bonds as Probes of the Folding Pathway of Barnase: Increasing the Stability Against the Rate of Denaturation. Biochemistry. 1993. vol. 32, pp. 4322-4329.*

Cho et al. Thermostable Variants of Bovine Beta-Lactoglobulin. Protein Engineering. 1994. vol. 7, No. 2, pp. 263-270.*

Chang, J-Y. Denatured States of Tick Anticoagulant Peptide. The Journal of Biological Chemistry. Jan. 1, 1999. vol. 274, No. 1, pp. 123-128.*

Chang, J-Y et al. Unfolding and Refolding of Cardiotoxin III Elucidated by Reversible Conversion of the Native and Scambled Species. Biochemistry. 1998. vol. 37, pp. 6745-6751.*

Chang, J-Y et al. The Disulfide Folding Pathway of Potato Carboxypeptidase Inibitor. Sep. 2, 1994. The Journal of Biological Chemistry. 269, 35, 22087-22094.*

Chang et al. Production of disulfide-linked hirudin dimer by in vitro folding. FEBS Letters. 1993. vol. 336, No. 1, pp. 53-56.*

Lu et al. Oxidative Folding of Murine Prion rPrP(23-231). European Journal of Biochemistry. 2001. vol. 268, pp. 3767-3773.*

Wickner et al. Posttranslational Quality Control: Folding, Refolding and Degrading Proteins. Science. Dec. 3, 1999. vol. 286, pp. 1888-1893.*

U.S. Appl. No. 11/177,509, Chang, filed Jul. 8, 2005, Non-Final Rejection (11 pages), Dated Apr. 10, 2007.

U.S. Appl. No. 11/177,509, Chang, filed Jul. 8, 2005, Amendment and Response to Office Action (32 pages), Dated Aug. 8, 2007.

U.S. Appl. No. 11/177,509, Chang, filed Jul. 8, 2005, Notice of Appeal (2 pages), Dated Apr. 29, 2008.

U.S. Appl. No. 11/177,509, Chang, filed Jul. 8, 2005, Amendment and Response to Final Office Action (9 pages), Dated Apr. 29, 2008.

Aguzzi, A. et al., "Progress and problems in the biology, diagnostics, and therapeutics of prion disease," *J. Clin. Invest.*, 114(2): 153-160 (2004).

Baker, J.T., "Material Safety Data Sheet for 2-Mercaptoethanol," *MSDA* No. M1209 http://jtbaker.com/msds/englishhtml/m1209.htm (Aug. 10, 2004).

(Continued)

*Primary Examiner*—Suzanne M. Noakes
(74) *Attorney, Agent, or Firm*—Ballard Spahr Andrews & Ingersoll, LLP

(57) ABSTRACT

Stable protein conformational isomers and methods for producing and isolating such isomers are disclosed. Methods of using such isomers, and products and compositions comprising such isomers are also disclosed.

34 Claims, 15 Drawing Sheets

OTHER PUBLICATIONS

Baker, J.T., "Material Safety Data Sheet for 2-Mercaptoethanol," *MSDA* No. M1209 http://jtbaker.com/msds/englishhtml/m1209.htm (Jul. 3, 2007).
Balter, M., "Disease Research: Prions: A lone killer or a Vital Accomplice," *Science*, 286(5440): 660-662 (1999).
Barrick, D. and Baldwin, R. L., "The molten globule intermediate of apomyoglobin and the process of protein folding," *Protein Sci.*, 2: 869-876 (1993).
Basler, K. et al., "Scrapie and Cellular PrP Isoforms Are Encoded by the Same Chromosomal Gene," *Cell*, 46: 417-428 (1986).
Bendheim, P.E. and Potempska, A., "Purification and Partial Characterization of the Normal Cellular Homologue of the Scrapie Agent Protein," *J. Infect. Dis.*, 158(6): 1198-1208 (1988).
Bendheim, P.E. et al., "Nearly ubiquitous tissue distribution of the scrapie agent precursor protein," *Neurology*, 42: 149-156 (1992).
Bessen, R.A. et al., "Non-genetic propagation of strain-specific properties of scrapie prion protein," *Nature*, 375: 698-700 (1995).
Biere, A.L. et al., "Parkinson's Disease-associated α-Synuclein Is More Fibrillogenic than β- and γ-Synuclein and Cannot Cross-seed Its Homologs," *J Biol Chem.*, 275(44): 34574-34579 (2000).
Blanco-Aparicio et al., "Potato Carboxypeptidase Inhibitor, a T-knot Protein, Is an Epidermal Growth Factor Antagonist That InhibitsT-tumor Cell Growth," *J. Biol. Chem.*, 273(20): 12370-12377 (1998).
Blundell, T.L., "Structure-based drug design," *Nature*, 384(7): 23-26 (1996).
Broach, J.R. and Thorner, J., "High-throughput screening for drug discovery," *Nature*, 384(7): 14-16 (1996).
Brown, H.R. et al., "The mRNA encoding the scrapie agent protein is present in a variety of non-neuronal cells," *Acta Neuropathol.*, 80: 1-6 (1990).
Campbell, I.D. and Bork, P., "Epidermal growth factor-like modules," *Curr. Opin. Struct. Biol.*, 3: 385-392 (1993).
Cashman, N.R. et al., "Cellular Isoform of the Scrapie Agent Protein Participates in Lymphocyte Activation," *Cell*, 61: 185-192 (1990).
Caughey, B. et al., "Strain-dependent Differences in β-Sheet Conformations of Abnormal Prion Protein," *J. Biol. Chem.*, 273(48): 32230-32235 (1998).
Caughey, B. et al., "Methods for Studying Prion Protein (PrP) Metabolism and the Formation of Protease-Resistant PrP in Cell Culture and Cell-Free Systems," *Mol. Biotechnol.*, 13: 45-55 (1999).
Chang, J-Y. and Li, L., "The Structure Of Denatured α-Lactalbumin Elucidated by the Technique of Disulfide Scrambling," *J. Biol. Chem.*, 276(13): 9705-9712 (2001).
Chang, J-Y. et al., "Analysis of the extent of unfolding of denatured insulin-like growth factor," *Protein Sci.*, 8: 1463-1468 (1999).
Chang, J-Y. and Li, L., "The Disulfide Structure of Denatured Epidermal Growth Factor: Preparation of Scrambled Disulfide Isomers," *J. Protein. Chem.*, 21(3): 203-213 (2002).
Chesebro, B. et al., "Identification of scrapie prion protein-specific mRNA in scrapie-infected and uninfected brain," *Nature*, 315: 331-333 (1985).
Clackson, T. et al., "Making antibody fragments using phage display libraries," *Nature*, 352: 624-628 (1991).
Cohen, F.E. and Prusiner, S.B., "Pathologic Conformations Of Prion Proteins," *Annu. Rev. Biochem.*, 67: 793-819 (1998).
Conway, K.A. et al., "Accelerated in vitro fibril formation by a mutant α-synuclein linked to early-onset Parkinson disease," *Nat. Med.*, 4(11): 1318-1320 (1998).
Cwirla, S.E. et al., "Peptides on phage: A vast library of peptides for identifying ligands," *Proc. Natl. Acad. Sci. USA*, 87: 6378-6382 (1990).
Daggett, V., "Structure-function aspects of prion proteins," *Curr. Opin. Biotechnol.*, 9: 359-365 (1998).
Dill, K.A. and Shortle, D., "Denatured States of Proteins," *Annu. Rev. Biochem.*, 60: 795-825 (1991).
Dobson, C.M., "Protein misfolding, evolution and disease," *TIBS*, 24: 329-332 (1999).
Donne, D.G., et al., "Structure of the recombinant full-length hamster prion protein PrP(29-231): The N terminus is highly flexible," *Proc. Natl. Acad. Sci. USA*, 94: 13452-13457 (1997).
Doolittle, R.F. et al., "Computer-based characterization of epidermal growth factor precursor," *Nature*, 307: 558-560 (1984).
Esch, F.S. et al., "Cleavage of Amyloid # Peptide During Constitutive Processing of Its Precursor," *Science*, 248(4959): 1122-1124 (1990).
Foster, B.A. et al., "Pharmacological Rescue of Mutant p53 Conformation and Function," *Science*, 286: 2507-2510 (1999).
Frand, A.R. et al., "Pathways for protein disulphide bond formation," *Trends Cell Biology*, 10(5): 203-210 (2000).
Gajdusek, D.C., "Unconventional Viruses and the Origin and Disappearance of Kuru," *Science*, 197(4307): 943-960 (1977).
Galfrè, G. and Milstein, C., "Preparation of Monoclonal Antibodies: Strategies and Procedures," *Methods Enzymol.*, 73(Pt. B): 3-46 (1981).
Gasset, M. et al., "Predicted α-helical regions of the prion protein when synthesized as peptides form amyloid," *Proc. Natl. Acad. Sci. USA*, 89: 10940-10944 (1992).
Griffith, J.S., "Self-replication and Scrapie," *Nature*, 215: 1043-1044 (1967).
Haile, M. et al., "Recent developments in tuberculosis vaccines," *Curr. Opin. Infec. Dis.*, 18: 211-215 (2005).
Hardy, J., "Amyloid, the presenilins and Alzheimer's disease," *TINS*, 20(4): 154-159 (1997).
Hashimoto, M. et al., "Role of Protein Aggregation in Mitochondrial Dysfunction and Neurodegeneration in Alzheimer's and Parkinson's Diseases," *Neuromolecular Med.*, 4(1-2): 21-35 (2003).
Hass, G.M. and Ryan, C.A., "Carboxypeptidase Inhibitor from Potatoes," *Methods Enzymol.*, 80: 778-791 (1981).
Hill, A.F. et al., "The same prion strain causes vCJD and BSE," *Nature*, 389: 448-450 (1997).
Hogan, J.C., "Directed combinatorial chemistry," *Nature*, 384(7): 17-19 (1996).
Holliger, P. et al., "'Diabodies': Small bivalent and bispecific antibody fragments," *Proc. Natl. Acad. Sci. USA*, 90: 6444-6448 (1993).
Horiuchi, M. and Caughey, B., "Prion protein interconversions and the transmissible spongiform encephalopathies," *Structure*, 7(10): R231-R240 (1999).
Hornemann, S. and Glockshuber, R., "A scrapie-like unfolding intermediate of the prion protein domain PrP(121-231) induced by acidic pH," *Proc. Natl. Acad. Sci. USA*, 95: 6010-6014 (1998).
Hornemann, S. et al., "Recombinant full-length murine prion protein, *m*PrP(23-231): purification and spectroscopic characterization," *FEBS Lett.*, 413: 277-281 (1997).
Ito, W. and Kurosawa, Y., "Development of an Artificial Antibody System With Multiple Valency Using an Fv Fragment Fused to a Fragment of Protein A," *J. Biol. Chem.*, 268(27): 20668-20675 (1993).
Jackson, G.S. et al., "Reversible Conversion of Monomeric Human Prion Protein Between Native and Fibrilogenic Conformations," *Science*, 283: 1935-1937 (1999).
James, T.L. et al., "Solution structure of a 142-residue recombinant prion protein corresponding to the infectious fragment of the scrapie isoform," *Proc. Natl. Acad. Sci. USA*, 94: 10086-10091 (1997).
Kessler, J.C. et al., "The N-terminal Repeat Domain of α-Synuclein Inhibits β-Sheet and Amyloid Fibril Formation," *Biochemistry*, 42: 672-678 (2003).
Klucken, J. et al., "Hsp70 Reduces α-Synuclein Aggregation and Toxicity," *J. Biol. Chem.*, 279(24): 25497-25502 (2004).
Kocisko, D.A. et al., "Cell-free formation of protease-resistant prion protein," *Nature*, 370: 471-474 (1994).
Koren, E. et al., "Characterization of a monoclonal antibody that binds equally to all apolipoprotein and lipoprotein forms of human plasma apolipoprotein B., I. Specificity and binding studies," *Biochim. Biophys. Acta.*, 876: 91-100(1986).
Kretzschmar, H.A. et al., "Scrapie Prion Proteins Are Synthesized in Neurons," *Am. J. Pathol.*, 122: 1-5 (1986).
Kretzschmar, H.A. et al., "Molecular Cloning of Human Prion Protein cDNA," *DNA*, 5(4): 315-324 (1986).
Kuwajima, K., "The Molten Globule State as a Clue for Understanding the Folding and Cooperativity of Globular-Protein Structure," *Proteins. Struct. Funct. Genet.*, 6: 87-103 (1989).
Liao, Y.J. et al., "Human Prion Protein cDNA: Molecular Cloning, Chromosomal Mapping, and Biological Implications," *Science*, 233(4761): 364-367 (1986).

Lowman, H.B. et al., "Selecting High-Affinity Binding Proteins by Monovalent Phage Display," *Biochemistry*, 30: 10832-10838 (1991).
Lu, B-Y. et al., "Isolation of Isoforms of Mouse Prion Protein with $PrP^{sc}$-like Structural Properties," *Biochemistry*, 40: 13390-13396 (2001).
Maiti, N.C. et al., "Raman Spectroscopic Characterization of Secondary Structure in Natively Unfolded Proteins: α-Synuclein," *J. Am. Chem. Soc.*, 126: 2399-2408 (2004).
Maiti, N.R. and Surewicz, W.K., "The Role of Disulfide Bridge in the Folding and Stability of the Recombinant Human Prion Protein," *J. Biol. Chem.*, 276(4): 2427-2431 (2001).
Matthews, C.R., "Pathways of Protein Folding," *Ann. Rev. Biochem.*, 62: 653-683 (1993).
Meyer, R.K. et al., "Separation and properties of cellular and scrapie prion proteins," *Proc. Natl. Acad. Sci. USA*, 83: 2310-2314 (1986).
Montelione, G.T. et al., "Solution Structure of Murine Epidermal Growth Factor Determined by NMR Spectroscopy and Refined by Energy Minimization with Restraints," *Biochemistry*, 31: 236-249 (1992).
Munishkina, L.A. et al., "Role of Protein—Water Interactions and Electrostatics in α-Synuclein Fibril Formation," *Biochemistry*, 43: 3289-3300 (2004).
Oesch, B. et al., "A Cellular Gene Encodes Scrapie PrP 27-30 Protein," *Cell*, 40: 735-746 (1985).
Price, D.L., "New order from neurological disorders," *Nature*, 399(24): A3-A5 (1999).
Prusiner, S.B., "Prions," *Proc. Natl. Acad. Sci. USA*, 95: 13363-13383 (1998).
Prusiner, S.B., "Novel Proteinaceous Infectious Particles Cause Scrapie," *Science*, 216(4542): 136-144 (1982).
Prusiner, S.B. et al., "Attempts to restore scrapie prion infectivity after exposure to protein denaturants," *Proc. Natl. Acad. Sci. USA*, 90: 2793-2797 (1993).
Prusiner, S.B. et al., "Prion Diseases and the BSE Crisis," *Science*, 278: 245-251 (1997).
Puckett, C. et al., "Genomic Structure of the Human Prion Protein Gene," *Am. J. Hum. Genet.*, 49: 320-329 (1991).
Riek, R. et al., "NMR characterization of the full-length recombinant murine prion protein, *m*PrP(23-231)," *FEBS Letters*, 413: 282-288 (1997).
Riek, R. et al., "NMR structure of the mouse prion protein domain PrP(121-231)," *Nature*, 382: 180-182 (1996).
Rydel, T.J. et al., "The Structure of a Complex of Recombinant Hirudin and Human #-Thrombin," *Science*, 249(4966): 277-280 (1990).
Safar, J. et al., "Eight prion strains have $PrP^{Sc}$ molecules with different conformations," *Nat. Med.*, 4(10): 1157-1165 (1998).
Schlessinger, J. and Ullrich, A., "Growth Factor Signaling by Receptor Tyrosine Kinases," *Neuron*, 9: 383-391 (1992).
Selkoe, D.J., "Translating cell biology into therapeutic advances in Alzheimer's disease," *Nature*, 399(24): A23-A31 (1999).
Selkoe, D.J. and Schenk, D., "Alzheimer's Disease: Molecular Understanding Predicts Amyloid-Based Therapeutics," *Annu. Rev. Pharmacol. Toxicol.*, 43: 545-584 (2003).
Shoji, M. et al., "Production of the Alzheimer Amyloid # Protein by Normal Proteolytic Processing," *Science*, 258(5079): 126-129 (1992).
Sifers, R.N., "Defective protein folding as a cause of disease," *Nat. Struct. Biol.*, 2(5): 355-357 (1995).
Sinclair, J.F. et al., "Kinetic partitioning during protein folding yields multiple native states," *Nat. Struct. Biol.*, 1(5): 320-326 (1994).
Sisodia, S.S. et al., "Evidence that #-Amyloid Protein in Alzheimer's Disease is not Derived by Normal Processing," *Science*, 248(4954): 492-495 (1990).
Sparkes, R.S. et al., "Assignment of the human and mouse prion protein genes to homologous chromosomes," *Proc. Natl. Acad. Sci. USA*, 83(19): 7358-7362 (1986).
Stahl, N. et al., "Structural Studies of the Scrapie Prion Protein Using Mass Spectrometry and Amino Acid Sequencing," *Biochemistry*, 32: 1991-2002 (1993).
Swietnicki, W. et al., "Aggregation and Fibrillization of the Recombinant Human Prion Protein huPrP90-231," *Biochemistry*, 39: 424-431 (2000).
Swietnicki, W. et al., "Familial Mutations and the Thermodynamic Stability of the Recombinant Human Prion Protein," *J. Biol. Chem*, 273(47): 31048-31052 (1998).
Swietnicki, W. et al., "pH-dependent Stability and Conformation of the Recombinant Human Prion Protein PrP(90-231)," *J. Biol. Chem.*, 272(44): 27517-27520 (1997).
Tanford, C., "Protein Denaturation," *Adv. Protein Chem.*, 23: 121-282 (1968).
Thomas, P.J. et al., "Defective protein folding as a basis of human disease," *TIBS*, 20: 456-459 (1995).
Timasheff, S.N. and Arakawa, T., "Stabilization of protein structure by solvents," In: Creighton, T.E., ed. *Protein structure: a practical approach. NY, IRL Press*, pp. 331-345 (1989).
Turk, E. et al., "Purification and properties of the cellular and scrapie hamster prion proteins," *Eur. J. Biochem.*, 176: 21-30 (1988).
Vagelos, P.R., "Are Prescription Drug Prices High?" *Science*, 252(5009): 1080-1084 (1991).
Weissmann, C. and Aguzzi, A., "Bovine spongiform encephalopathy and early onset variant Creutzfeldt-Jakob disease," *Curr. Opin. Neurobiol.*, 7: 695-700 (1997).
Will, R.G. et al., "Deaths from variant Creutzfeldt-Jakob disease," *Lancet*, 353(9157): 979 (1999).
Woody, R.W., "Circular Dichroism," *Methods in Enzymol.*, 246: 34-71 (1995).
Yu, M-H. et al., "The Z type variation of human $\alpha_1$-antitrypsin causes a protein folding defect," *Nat. Struct. Biol.*, 2(5): 363-367 (1995).
Zhang, H. et al., "Physical Studies of Conformational Plasticity in a Recombinant Prion Protein," *Biochemistry*, 36: 3543-3553 (1997).
Zhu, M. and Fink, A.L., "Lipid Binding Inhibits α-Synuclein Fibril Formation," *J. Biol. Chem.*, 278(19): 16873-16877 (2003).
U.S. Appl. No. 11/177,509, Chang, filed Jul. 8, 2005, Non-Final Rejection, Dated Dec. 16, 2008.

* cited by examiner $PrP^C$ $PrP^{Sc}$

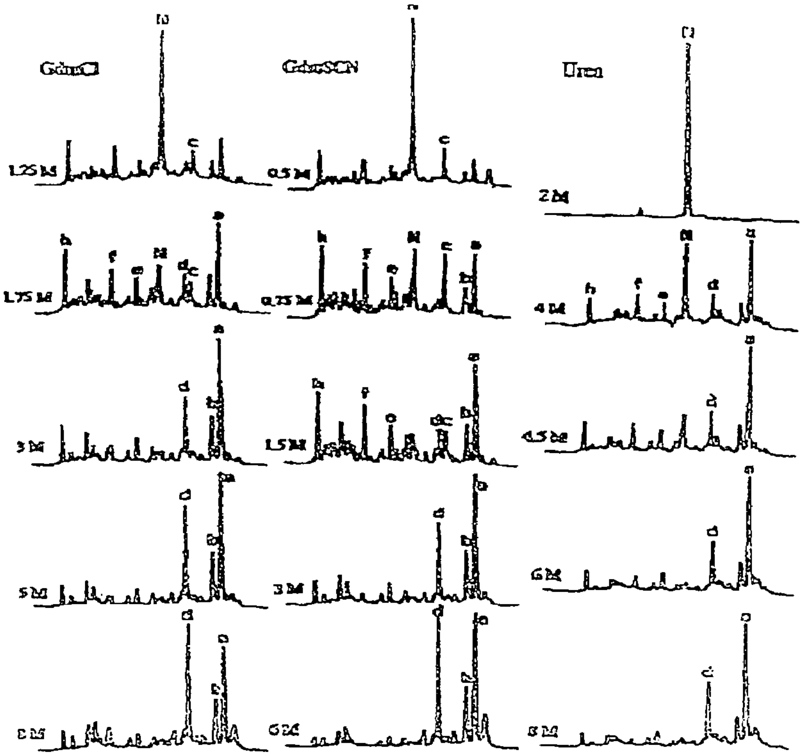
FIGURE 11
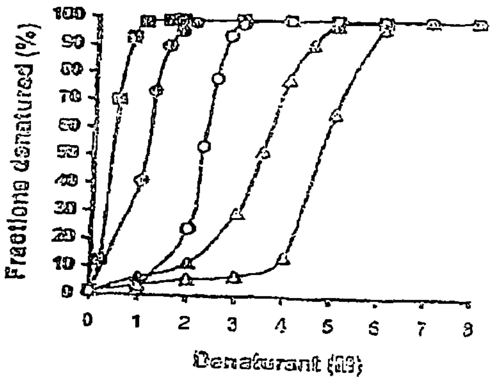

PROTEIN CONFORMATIONAL ISOMERS, METHODS OF MAKING, METHODS FOR USING, COMPOSITIONS COMPRISING AND PRODUCTS MADE THEREWITH

RELATED APPLICATION DATA

The present application claims priority of U.S. Provisional Application Ser. No. 60/309,543, filed Aug. 1, 2001, entitled "Protein Conformational Isomers, Methods for Producing, Methods for Using, and Compositions and Products Made Therefrom."

BACKGROUND OF THE INVENTION

1. Field of the Invention

The present invention relates to conformational protein isomers, to methods of producing and isolating such isomers, to methods of utilizing such isomers, and to products comprising and products made from such isomers. In another aspect, the present invention relates to conformational protein isomers having at least one disulfide bond, to methods of producing and isolating such disulfide isomers, to methods of utilizing such disuflide isomers, and to products comprising and products made from such disulfide isomers.

2. Description of the Related Art

A protein can potentially assume an exceedingly large number of conformations. Under physiological conditions, a protein usually folds "properly" and adopts the native structure with a well defined three dimensional conformation. Unlike the native protein, a denatured protein consists of a collection of conformational isomers that exist in a state of equilibrium. Conformational isomers of denatured proteins are rich in number and varied in shape. Conformational isomers represent an opulent resource of biological molecules that have, thus far, remained untapped. The major obstacle in utilizing the untapped potential of conformation isomers is the inherent difficulty in the isolation and characterization of pure conformational isomers, not only because of the excessive large number that may exist but also because of their instability and rapid inter-conversion.

One conventional approach used to study protein folding is to unfold proteins in the presence of a strong denaturant, such as 8M urea or 6. m GdmCl, by extreme pH, or by high temperature. Following the removal of the denaturant, reduction of pH, or reduction of temperature, the denatured proteins usually refold spontaneously to form the native structure. The refolding pathway of the protein is monitored by the restoration of at least one physicochemical signal that distinguish the native and unfolded states. Commonly used signals are spectra of fluorescence, circular dichroism, infrared, ultraviolet light and NMR coupled with amide proton exchange. Unfortunately, in most cases this method does not permit isolation of folding intermediates.

Another conventional method use to study protein folding is oxidative folding of disulfide containing proteins. Proteins are reduced and denatured in the presence of reducing agent, such as dithiothreitol, and denaturant, such as 6M GdmCl. After exclusion of the reductant and denaturant, the reduced and denatured protein is allowed to refold in the presence of redox buffer. The refolding pathway is then tracked by the mechanisms of formation of the native disulfide bonds. For example, a protein that contains three disulfide bonds can potentially assume 75. different disulfide isomers (15. isomer species having one disulfide bond, 45. having two disulfide bonds, and 15. having three disulfide bonds). The disulfide folding pathway is characterized by the heterogeneity and structures of the disulfide isomers that accumulate in the process of oxidative folding that leads to formation of the native structure. However, without chemical modification, the method of oxidative folding does not generate stable isomers.

In spite of advancements in the art, methods for generating large numbers of stable conformational isomers of a protein have not been developed. Thus, there remains a need for methods for producing large numbers of stable conformational isomers of a protein.

There is another need in the art for purified populations of stable conformational isomers of a protein.

There is even another need in the art for methods for screening and identifying therapeutic agents/drugs wherein the agent is a disulfide isomer.

There is still another need in the art methods for screening and identifying therapeutic agents/drugs wherein the agent is a protein stabilizer.

There is yet another need in the art for methods of investigating the molecular mechanisms of a conformational disease.

There is even still another need in the art for compositions and products comprising protein conformational isomers.

There is even yet another need in the art for methods for treating a patient afflicted with a conformation disease.

These and other needs will become apparent to those of skill in the art upon review of this specification, including its drawings and claims.

SUMMARY OF THE INVENTION

It is an object of the present invention to provide methods for producing large numbers of stable conformational isomers of a protein.

It is another object of the present invention to provide purified populations of stable conformational isomers of a protein.

It is even another object of the present invention to provide methods for screening and identifying therapeutic agents/drugs wherein the agent is a disulfide isomer.

It is still another object of the present invention to provide methods of screening and identifying therapeutic agents/drugs wherein the agent is a protein stabilizer.

It is yet another object of the present invention to provide methods of investigating the molecular mechanisms of a conformational disease.

It is even still another object of the present invention to provide compositions and products comprising protein conformational isomers.

It is even yet another object of the present invention to provide methods for treating a patient afflicted with a conformation disease.

According to one embodiment of the present invention there is provided a method for generating conformational isomers of a disulfide bond-containing native protein. Generally the method comprises denaturing a disulfide bond-containing native protein in a denaturing buffer to produce a mixture comprising a mixed population of fully oxidized conformational isomers. Generally the buffer comprises a denaturant. Preferably the buffer comprises a denaturant and a thiol agent. The denaturant is selected from the group consisting of urea, GdmCl, GdmSCN, organic solvents, and elevated temperature. The thiol agent is selected from the group consisting of 2-mercaptoethanol, reduced glutathione and cysteine. The isomers comprise at least one disulfide bond, and at least one disulfide bond of each of the isomers is in a different conformation from that of the disulfide bonds of the native protein. That is to say, at least one of the disulfide bonds of each of the isomers is a non-native disulfide bond. The at least one disulfide bond and the at least one non-native disulfide bond may be the same disulfide bond. Preferably the native protein and disulfide isomers each comprise at least two disulfide bonds.

According to another embodiment of the present invention there is provided a method for amplifying a particular conformational isomer species. Generally the method comprises the step of: a) denaturing a disulfide bond-containing native protein in a denaturing buffer to produce a mixture comprising a mixed population of fully oxidized disulfide bond-containing conformational isomers, wherein the isomer proteins of each species of isomers comprise at least one disulfide bond. Preferably the at least one of the disulfide bond of is a non-native disulfide bond. Preferably the isomer proteins of each species of isomers comprise at least two disulfide bonds. The method further comprises the steps of: b) isolating a desired isomer species from the mixture; and c) subjecting the remaining portion of the mixture to steps a) and b) in order to generate more of the desired conformational isomer species, and to isolate more of the desired species. The desired species can be any of the species of isomer proteins of the mixture. The method may also further comprise the step of: d) repeating steps a), b), and c) until a desired quantity of the desired isomer species has been obtained. Any technique known in the art for isolating a target protein from a heterogeneous mixture may be utilized herein. In a preferred embodiment, the technique of isolating performed in step b) comprises passing the mixture through an affinity column, wherein the column comprises immobilized molecules having affinity to the desired isomer species, and thus the desired isomer species is retained by the column. The unbound mixture comprising unbound isomer species is then eluted from the column.

According to even another embodiment of the present invention there are provided conformational protein isomers generated by the methods of the invention. The isomers may be a single species of isomer, or may be a mixed population of isomers. The isomers may be purified or partially purified and all methods known to one of skill in the art for purifying proteins are applicable. Because the disulfide scrambling method and isomer amplification method of the invention may be used on any native disulfide-containing protein, the isomers of the invention may be isomers of any protein which has been subjected to the present scrambling and/or amplification methods. Generally the isomer comprises at least one disulfide bond and si a conformation isomer of the native protein, and the at least one disulfide bond is a non-native disulfide bong. Preferably, the isomer proteins each comprise at least two disulfide bonds. Particularly preferred isomers of the invention include isomers of the prion protein ($PrP^c$), α-lactalbumin, epidermal growth factor, and potato carboxypeptidase inhibitor.

According to still another embodiment of the present invention there are provided methods of screening for therapeutic agents wherein the agent is a disulfide isomer. Generally the method comprises the steps of: scrambling a native protein as described above; and identifying isomers within the resulting scrambled isomers which function either as agonists or antagonists of the activity/function of the native protein.

According to yet another embodiment of the present invention there is provided a method of screening the potency of protein stabilizers. Generally the method involves contacting an amount of an agent together with at least one disulfide isomer and assaying whether the agent causes the non-native conformation of isomer to return to the native conformation. The agent may be any known protein stabilizer or any agent found to function as a protein stabilizer using the present method.

According to even still another embodiment of the present invention there is provided a method for elucidating the molecular mechanisms underlying conformational diseases and for identifying the proteins and protein conformation associated with such diseases. Generally the method of the invention useful for identifying a protein associated with disease comprises the step of a) assaying the ability of a protein to promote disease in a cellular system, wherein said protein is an isomer protein of the invention.

According to even yet another embodiment of the invention there are provided compositions comprising at least one disulfide isomer wherein said isomer is a conformational isomer of a disulfide-containing native protein, and wherein said isomer and native protein differ only in their conformation and in the pairing of cysteine amino acid residues of at least one of their disulfide bonds, preferably at least two of their disulfide bonds. Generally the composition of the invention is produced by denaturing a disulfide-containing native protein in a denaturing buffer to produce a mixture of fully oxidized conformational isomers comprising at least one disulfide bond, wherein said buffer comprises a thiol agent and a denaturant. Preferably the isomers of the mixture comprise at least two disulfide bonds.

According to still even another embodiment of the present invention there are provided methods of treating a patient. Generally the method comprises administering an effective dose of a composition of the invention to a patient afflicted with a protein conformation-associated disorder. The patient may be afflicted with any conformation-associated disorder such as, for example, any prion-associated disease, mad cow disease, scrapie in sheep, Creutzfeldt-Jacob disease and familial insomnia in human, Alzheimer disease, $a_1$-antitrypsin deficiency and cystic fibrosis. The patient may be any mammal, preferably a human.

These and other embodiments of the present invention will become apparent to those of skill in the art upon review of this specification, including its drawings and claims.

BRIEF DESCRIPTION OF THE DRAWINGS

FIG. 11 provides the thermodynamic denaturation of α-lactalbumin by different concentrations of different denaturants.

DETAILED DESCRIPTION OF THE INVENTION

The present invention is directed to conformational protein isomers, methods of making such isomers, methods of using such isomers, and compositions and products made from such isomers. With respect to function/activity, the conformational isomers may have less, more, or about the same activity as the native protein. Thus, depending on the conformation and specific activity of the isomer, the isomer may function as an agonist, or as an antagonist to the native protein. These agonists and antagonists may be used as therapeutic agents useful in treating a patient afflicted with a conformational disease.

The isomers and methods of the present invention are useful as research tools in areas such as, for example, screening for novel drugs and therapeutic compounds, developing and elucidating models for protein folding and for protein conformation-associated disorders, and for generating protein libraries. The isomers and methods of the present invention are also useful in developing pharmaceutical/therapeutic agents for the treatment of patients afflicted with disorders associated with protein conformational isomers.

Figure 1:
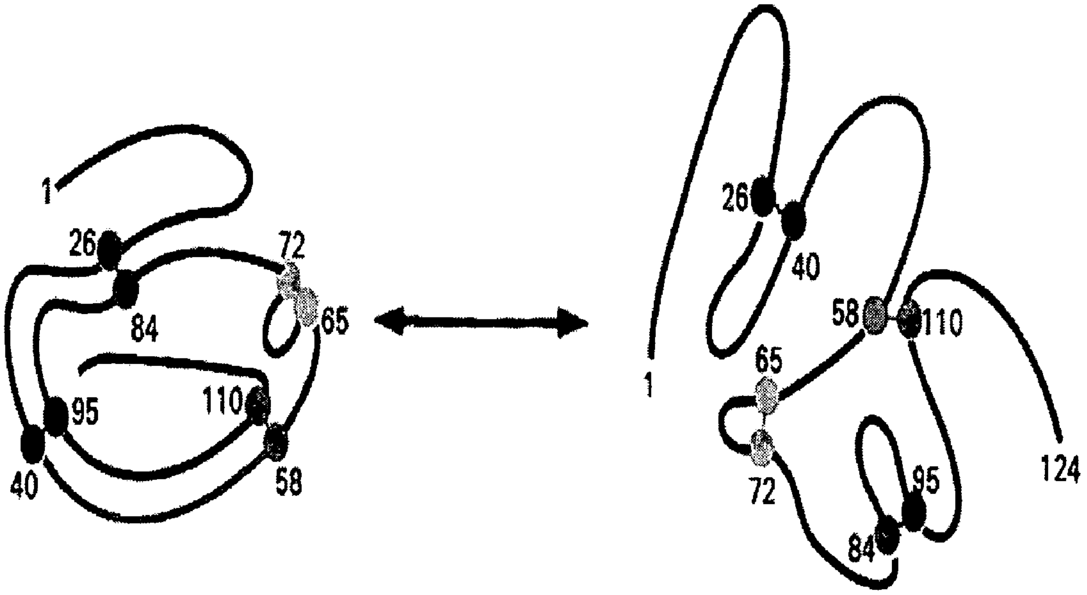
FIG. 1 is a schematic comparison between a protein containing four disulfide bonds in the native configuration (on left) and in a scrambled configuration (on right).

The present invention for producing conformational isomers is based on the present inventor's inventive technique of disulfide scrambling. The inventor has found that in the presence of a denaturant and a thiol initiator, a disulfide-containing native protein will become denatured and its native disulfide bonds become "shuffled" relative to the native disulfide bonds. Thus the disulfide scrambling process of the invention converts a native protein into a mixture of heterogeneous scrambled disulfide isomer species that are stable in their non-native confirmation due to the non-native disulfide bonds therein, as illustrated in FIG. 1. This process of denaturation can be fine-tuned, controlled, and halted at any time point by acidification, or by removal of the thiol initiator. One convenient aspect of the invention is that upon removal of the denaturant but retention of the thiol initiator, the scrambled isomers spontaneously refold to form the native structure by reshuffling their non-native disulfide bonds.

As used herein, the term "disulfide" is defined to be the bond formed between a sulfhydryl group of one cysteine amino acid reside, and a sulfhydryl group of a second cysteine amino acid residue. The two cysteine residues bound together by a disulfide are referred to as a "cystine" residue. As used herein, the term "disulfide" is equivalent to and interchangeable with disulfide bond, disulfide bridge, disulfide crosslink, and all other applicable terms and phrases known and used by one of skill in the art.

As used herein, the term "conformation" is defined to be the spatial arrangement of amino acid residues of a protein/peptide. As used herein, the term "conformation" is equivalent to and interchangeable with tertiary structure, three-dimensional structure, spatial arrangement, and all other applicable terms and phrases known and used by one of skill in the art. As used herein the term "conformational disease" is defined to mean a disease which results from non-native conformation of a protein.

As used herein, the term "native disulfide" is defined to be a disulfide in a protein resulting from the pairing between a sulfhydryl group on one cysteine residue with a sulfhydryl group on a second cysteine residue, wherein such pairing is native pairing of sulfhydryl groups (i.e., native pairing of cysteine amino acid residues) and exists in the native conformation of a protein. As used herein, the term "non-native disulfide" is defined to be a disulfide in a protein resulting from the pairing between a sulfhydryl group on one cysteine residue with a sulfhydryl group on a second cysteine residue wherein such pairing is non-native pairing of sulfhydryl groups (i.e., non-native pairing of cysteine amino acid residues) and does not exist in the native conformation of a protein. Thus, a non-native disulfide would exist in the scrambled disulfide isomers of the invention.

As used herein, "scrambled disulfide isomer" and "scrambled isomer" are defined to mean a conformational isomer of a native protein wherein the isomer comprises at least one non-native disulfide, preferably at least two non-native disulfides, and the isomer has a non-native protein conformation. (Note the scrambled isomers may also comprise native disulfides in addition to the at least one non-native disulfide.) Each different species of scrambled isomer of the invention has a unique species-specific protein conformation and each of the species differ from one another by at least one non-native disulfide. That is, each of the species of protein isomers contains at least one unique pairing of cysteine residues wherein the pairing is not found in the other species or in the native protein. Preferably the isomers of the invention differ from one another and from the native protein by at least two non-native disulfide and thus have at least two species-specific pairings of cysteine residues.

Figure 2:
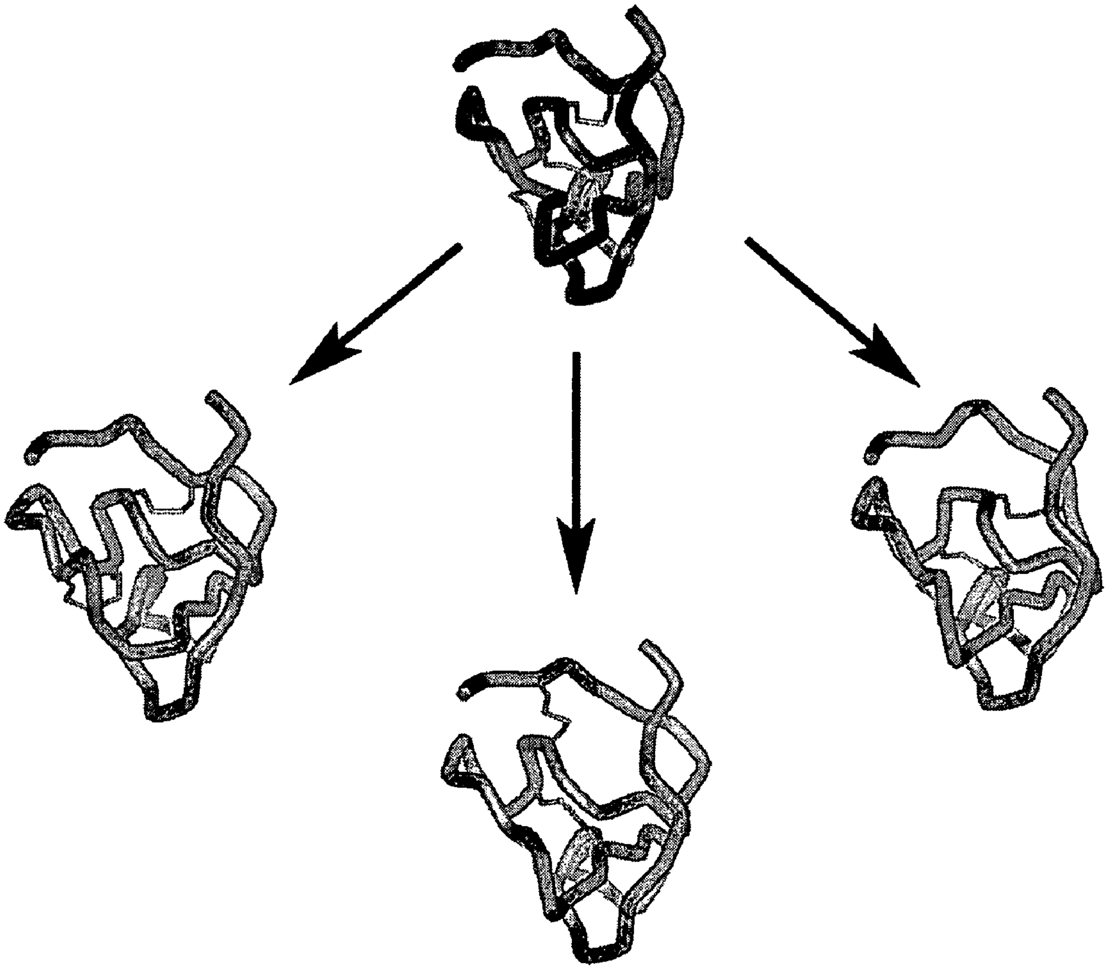
FIG. 2 illustrates design of conformational isomers of hirudin.
Figure 13:
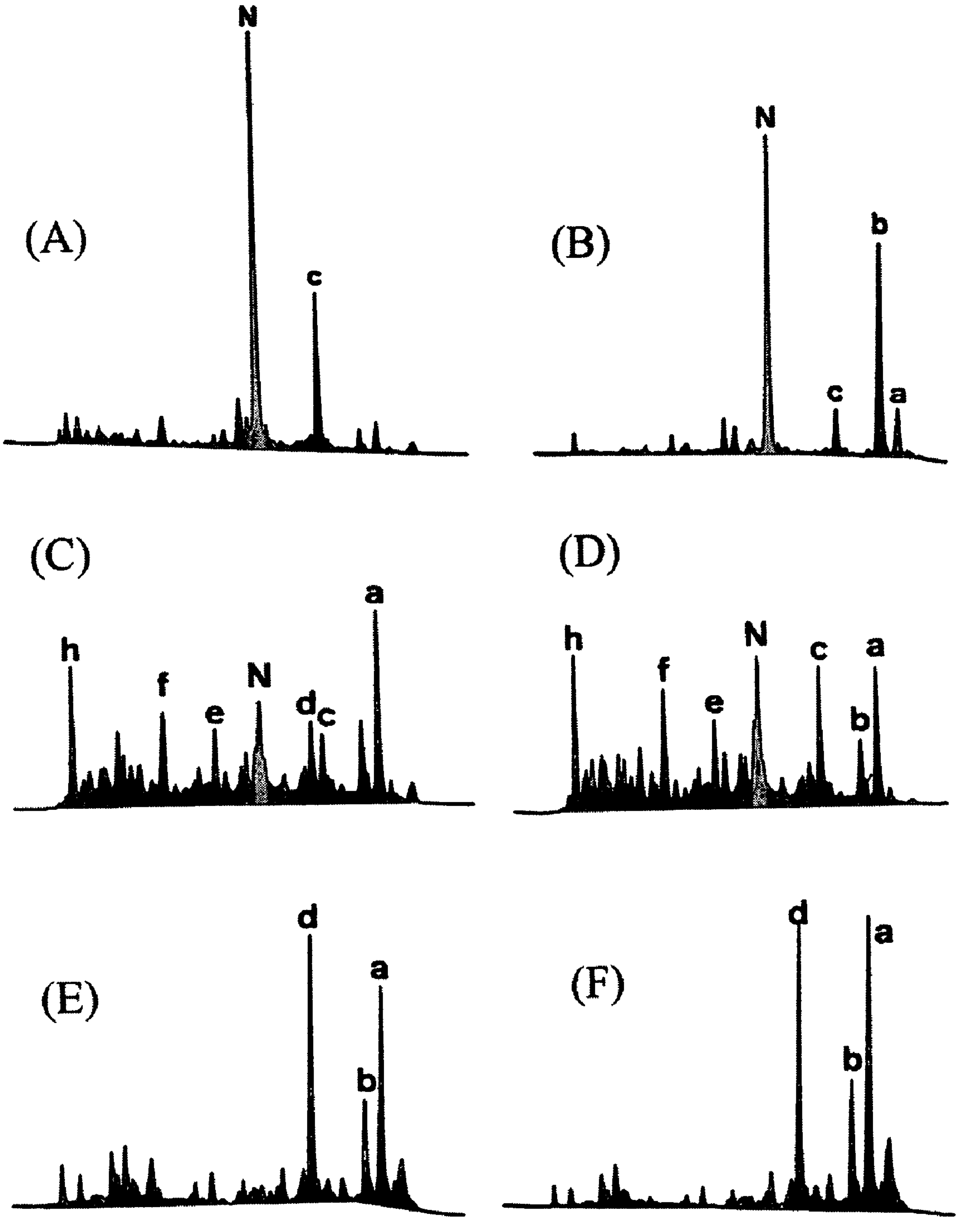
FIGS. 13(4A-4F) show HPLC profiles of selected populations of scrambled isomers of α-lactalbumin prepared by denaturing the native protein under different conditions.

The numerous advantageous features of the technique of disulfide scrambling for the preparation of denatured isomers include: the sheer large number of structurally defined isomers that can be generated, as shown in Table 1;. the possibility of increasing the number and diversity of denatured isomers by genetically engineering cysteine residues in a target protein (FIGS. 2 and 10) selection of specific denaturing conditions (FIGS. 13 and 14); and the potential for rationale design of desirable conformational isomers, for instance, through the addition, deletion, replacement, and/or shifting in the sequence position of a cysteine residue(s) (FIG. 2).

Shown in FIG. 2 is hirudin, a thrombin specific inhibitor isolated from leech, discussed to more clearly illustrate how a protein's cysteine residues may be mutated/modified to produce isomers with activity levels different from that of the native protein. The N-terminal region of hirudin is structurally mobile and is part of the functional site which binds to the active site of thrombin. The potency and specificity of hirudin can potentially be altered by adjusting the mobility of its N-terminal region. Normally, amino acid residue cysteine 6. (Cys6) of hirudin forms a native disulfide bond with amino acid residue cysteine 14. (Cys14). By changing the sequence position of Cys6, for example by use of site-directed mutagenesis, it is possible to create hirudin isomers with either increased or decreased function relative to the N-terminal region. That is, by performing the present inventive disulfide scrambling and/or amplification technique on a mutant hirudin protein containing mutation in the sequence position of amino acid residue Cys6, it is possible to create hirudin isomers having strengthened rigidity of the N-terminal region, as well as mutant hirudin proteins having weakened rigidity of the N-terminal region (FIG. 2).

The disulfide scrambling process of the present invention also presents numerous advantages for characterizing denatured proteins. The scrambled disulfide isomers are intra-crosslinked by the non-native disulfides thus forming disulfide loops of various sizes, the isomers are not inter-convertible into one another in the absence of thiol catalyst or acidic pH. Because of their stability, diverse conformations, and varying physicochemical properties, scrambled isomers can be separated and purified by liquid chromatography, and structurally characterized. This allows one to fine-tune the production of the isomers and produce a desired number of different conformational isomer species, each species having a stable species-specific structure.

Another of the numerous advantages of the present invention is that the process of denaturation can be monitored in a time-course manner by structural characterization of acid trapped intermediate(s). This permits kinetic analysis of the chemical process of protein denaturation and identification of structurally defined intermediates present in the denaturation pathway of a given protein.

There are a wide variety of applications for the technology of the present invention. For example, the ability to generate large numbers of protein conformational isomers with defined structures has immense value for drug research for discovery and development of novel drugs. The present invention is also directed to a protein library of conformational isomers useful for the screening of active antagonist or agonists of a target protein.

The ability provided by the present invention to monitor the chemical process of protein denaturation (i.e., conformational change) is of use in diagnosing diseases caused by protein conformational change, such as prion disease, and the molecular mechanisms underlying such diseases. For instance, the study of designer mutant cellular prion ($PrP^C$) proteins, wherein the mutation affects the presence or location of at least one cysteine residue of $PrP^C$, can be used to track the conformational change leading to the formation of the infectious structure ($PrP^{SC}$).

One embodiment of the present invention is directed to a method of generating conformational isomers of a native, target protein, wherein the disulfide bonds of the native protein are shuffled and the protein is converted into scrambled disulfide isomers. Generally the inventive method for producing isomers of a protein comprises denaturing a sample comprising a species of native proteins in a denaturing buffer under incubation conditions sufficient to produce a mixture comprising at least one species of isomer protein. Generally, the native proteins have a native conformation and comprise at least one disulfide bond. Preferably the native protein comprises at least two disulfide bonds. The disulfide bonds of the native protein are native disulfide bonds. The resulting mixture comprises at least one species of isomer proteins having a non-native conformation and comprising at least one non-native disulfide bond. Preferably the isomers comprise at least two non-native disulfide bonds. Generally the mixture comprises at least one species of isomer protein, preferably, the mixture comprises at least two species of protein isomers, and each of the species of protein isomers has its own signature or species-specific non-native conformation. Thus, each of the species of protein isomers differ from one another and from the native protein by their species-specific non-native conformation. Each species of isomer proteins also differ from one another and from the native protein by the pairing of cysteine amino acid residues in at least one, preferably at least two, of their non-native disulfide bonds.

For example if in the native conformation of a protein there were three disulfide bonds (native disulfide bonds by definition) and those three bonds were formed by pairings between Cys1-Cys2, Cys3-Cys4, and Cys5-Cys6. (for simplicity, the six cysteines of the example protein are numbered 1-6. but the native protein of the example would comprise far greater than 6. amino acid residues in total), then each disulfide isomer species of that native protein would have at least one, preferably two, different pairings. Examples of different pairings include, for example, Cys1-Cys3, Cys2-Cys4. and Cys5-Cys6, or Cys1-Cys4, Cys2-Cys5. and Cys3-Cys6, or Cys1-Cys5, Cys2-Cys4. and Cys3-Cys6, and all possible pairing combinations thereof.

Generally, the inventive method of disulfide scrambling comprises dissolving generally at least about 0.01. mg of a native protein at a concentration of about 0.01-5.0. mg/ml, in a volume generally of at least about 10. milliliters of alkaline buffer, also called denaturing buffer. Aside from practical limitations, the amount of native protein used in the reaction and the volume of the reaction have no minimum or maximum value limits, and their values are generally determined by the amount of protein available to the user, and the type of laboratory equipment available to the user. Thus, the amount of native protein used can range from 0.1. g to upwards of about 200. kg of native protein, and the amount of alkaline buffer (i.e, reaction volume) can range from about 100. microliters to as much as about 1000. liters.

Generally, the denaturing buffer of the invention comprises Tris-HCl at a concentration of from about 20. to about 200. mM, and at a pH of from about 7.0. to about 8.5.. Preferably, the buffer further comprises a denaturant. More preferably, the buffer also comprises a thiol initiator/catalyst.

One inventive aspect of the present invention is the use of the combination of a denaturant with an optimized concentration of a thiol initiator for converting a native protein into a mixture of fully oxidized scrambled isomers. Denaturants useful herein are any known in the art and include, for example, urea, GdmCl, GdmSCN, organic solvents, elevated temperature, extreme pH, surfactants and detergents, and mechanical forces such as shaking, shearing, ultrasound, radiation and pressure. Preferably, the denaturant is a chemical denaturant. Thiol initiators/agents useful herein are any such agents known in the art and include, for example, 2-mercaptoethanol, reduced glutathione, cysteine, and any other thiol-containing agent or chemical compound. Preferred thiol initiators/agents are 2-mercaptoethanol, reduced glutathione, and cysteine.

Generally the conditions for each of the denaturants useful in the denaturing buffer of the invention are as follows: urea—from about 1M to about 10. M; GdmCl—from about 1M to about 8M; GdmSCN—from about 1M to about 6M; and organic solvents at a concentration in a range of from about 1% to about 99% by volume. Conditions for thermal denaturation are generally elevated temperature in a range of from about 35° C. to about 70° C., for a time period ranging from 1. minute to 240. minutes, preferably from about 2. minutes to about 120. minutes, more preferably from about 3. minutes to about 70. minutes.

The denaturing reaction is allowed to reach equilibrium and is typically performed at a temperature in the range of about 0° C. to about 80° C., preferably at a temperature in the range of about 15° C. to about 50° C., more preferably at a temperature in the range of about 20° C. to about 40° C., and for a time period ranging from about 15. minutes to about 7. days, preferably from about 60. minutes to about 3. days.

Generally, the final concentration for each of the thiol agents useful in the denaturing buffer is as follows: 2-mercaptoethanol in the range of about 0.01. mM to about 0.5. mM, preferably in the range of from about 0.05. mM to about 0.4. mM, more preferably in the range of 0.1. mM to 0.3. mM; cysteine in the range of about 0.1. mM to about 5. mM, preferably in the range of from about 0.5. mM to about 2. mM; and reduced glutathione in the range of about 0.1. mM to about 5. mM preferably in the range of from about 0.5. mM to about 4. mM. Tailoring the type and amount of denaturant as well as the type and amount of thiol initiator may be necessary for production of a specific isomer species of a target protein.

To monitor the kinetics of denaturation and unfolding processes, aliquots of the sample being scrambled may be removed at various time intervals, quenched with trifluoroacetic acid, generally from about 1% TFA to about 10% TFA, preferably about 4% TFA, and analyzed by HPLC. The denatured and acidified sample is subsequently stored at a temperature of less than 0° C., preferably at about −20° C.

For large scale production of conformational isomers of the invention, the denaturant and thiol agent may be removed from the sample by gel filtration such as, for example, by use of PD-10. or NAP-5. columns from Pharmacia AG, or any other product or technique known by one of ordinary skill in the art to perform an equivalent function. Subsequent elution of the sample from the column is generally carried out using about 0.1% to about 10% TFA, preferably about 1% TFA. The resulting denatured scrambled isomers are stable at −20° C. indefinitely.

An exceedingly large number of conformational isomer species can be produced by the disulfide scrambling methods of the present invention. The number of possible scrambled isomer species generated by the method of the present invention is dependent upon at least the number of disulfide bonds in the protein, as shown in Table 1. (note in Table 1, the native configuration is included in the count). Studies with protein models containing 3. and 4. disulfide bonds have shown that denatured proteins comprise about 50% to about 80% of such possible disulfide isomers, although the isomer species may not be present in equal or comparable concentrations, exemplified by FIG. 3.

TABLE 1

Possible numbers of disulfide isomers/configurations based on the number of disulfide bonds in a native protein.

| # of disulfide bonds in a native protein | total possible # of different disulfide isomers* |
|---|---|
| 1 | 1 |
| 2 | 3 |
| 3 | 15 |
| 4 | 105 |
| 5 | 945 |
| 6 | 0395 |
| 7 | 135135 |
| 8 | 2027025 |
| 9 | 34459425 |
| 10 | 654729075 |

*The native configuration is included in the count.

Figure 3:
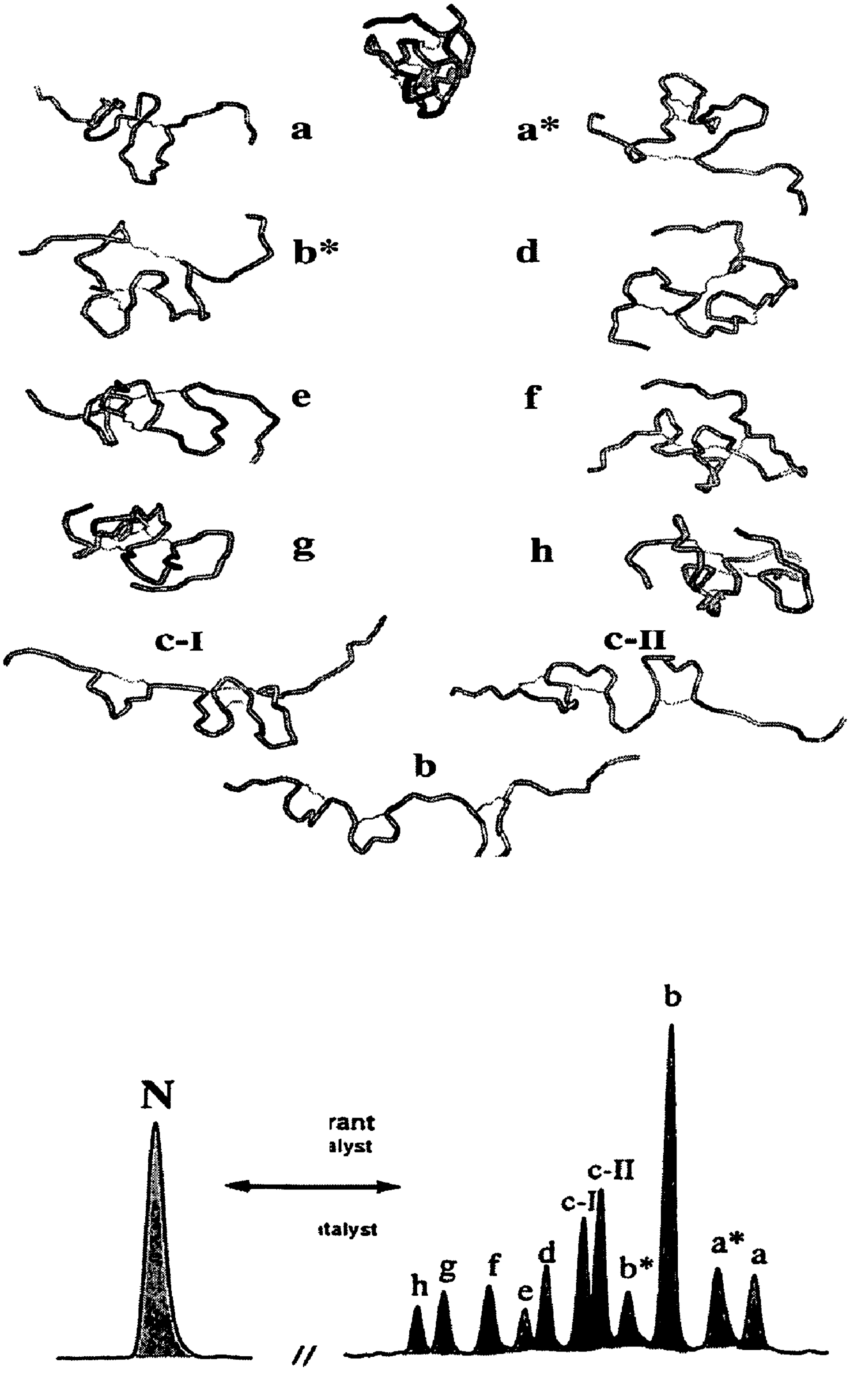
FIG. 3 depicts the conformations of a native protein and scrambled isomers thereof (top), and those proteins by HPLC (bottom).

Shown in FIG. 3 are denatured scrambled isomers (a, a*, b, b*, c-I, c-II, d, e, f, g, h) of the native (N) hirudin protein prepared by the present scrambling method. They differ for one another by disulfide orientation and protein conformation (depicted in top portion) and in most cases, the isomers and native protein can be separated and isolated by HPLC (depicted in bottom portion).

To further increase the number of possible scrambled isomers of a target protein, additional disulfide bonds can be introduced through site-directed mutagenesis. Any technique for site-direct mutagenesis known in the art may be used herein. The diversity of the scrambled isomers produced by the process of the present invention may also be further increased by the deletion of, replacement of, or shifting of the sequence position of a cysteine residue in a protein. In other words, by creating a mutant protein wherein the mutation comprises altering the location or presence of a cysteine residue, it is possible to increase the number of resulting isomer species.

Figure 4:
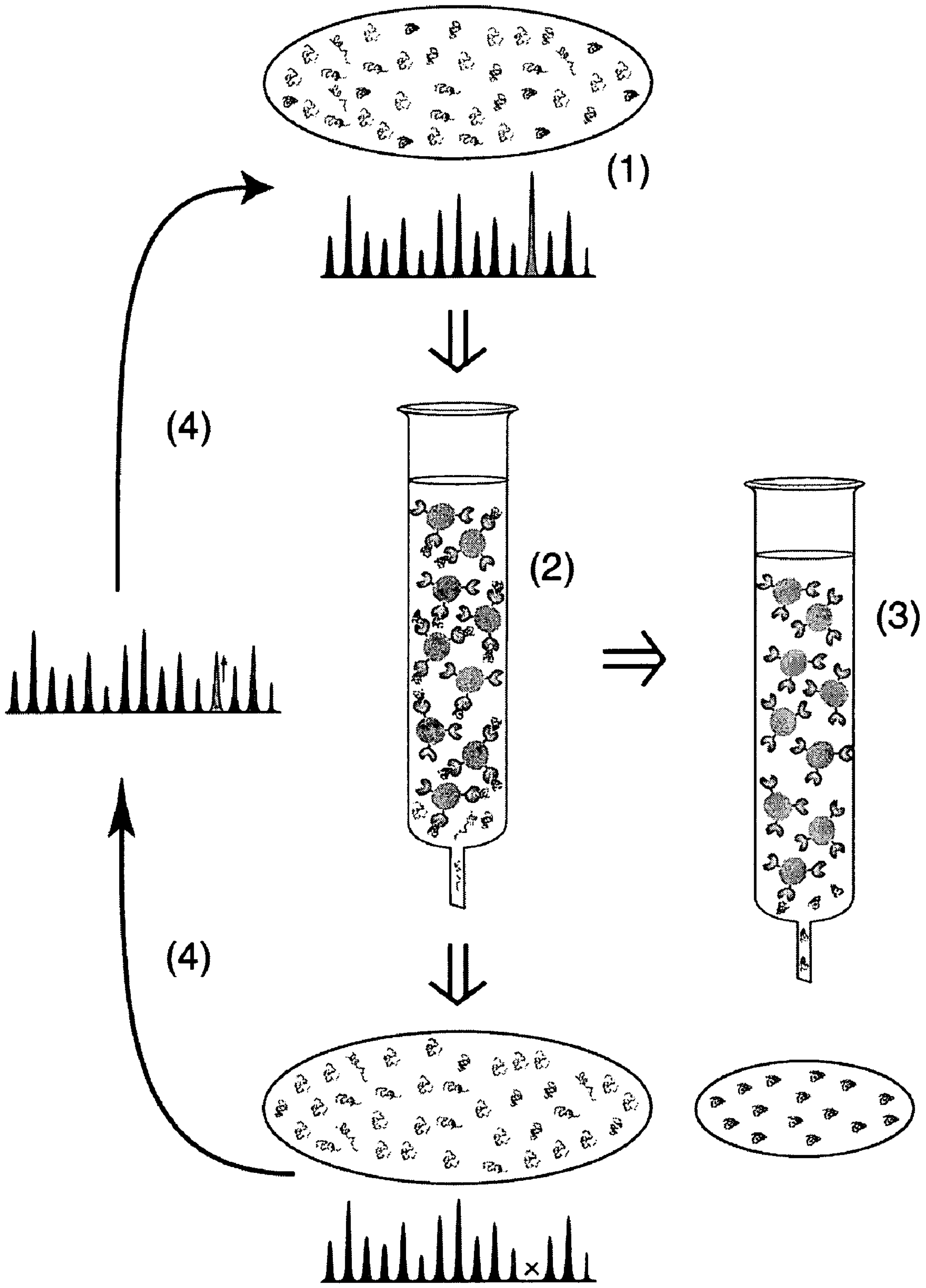
FIG. 4 outlines the steps of the process of recycling of the equilibration of disulfide isomers for the production of active isomers.

Another embodiment of the invention is directed to a method for the amplification and isolation of a desired/targeted isomer species within the mixed population of scrambled isomers. The method is based on recycling of the equilibration of disulfide isomers. A schematic representation of this strategy is shown in FIG. 4. Generally, the process comprises the step (1) of preparing a mixed population of isomers from a native protein, wherein the population comprises different disulfide isomer species. This step may be carried out by using the disulfide scrambling method of the invention. Numerous different species of disulfide isomers exist in a state of equilibrium within the resulting disulfide isomer population. A targeted/desired isomer species is then targeted for isolation and purification as shown in step (2). Isolation may be carried out by any technique known in the art for purifying a single protein species from a heterogeneous mixture. In a preferred embodiment, the mixed population of disulfide isomers are passed through an affinity column wherein the desired isomer species is targeted for retention on the column via immobilized receptor, or antibody, or any other molecule specific for binding to the desired isomer species. The desired isomers (indicated as filled circles in FIG. 4) bound to the receptor will be retained on the column. The remaining unbound isomer species, referred to herein as the "remaining sample", is eluted from the column.

AS shown in step (3) of FIG. 4, the desired isomers which are retained/bound on the column are then isolated and recovered using techniques known by one of skill in the art for isolating and recovering proteins from a column, such as, for example, eluting with an elution buffer comprising high salt concentration, or extreme pH. The disulfide structures and other physicochemical properties of the isolated protein isomers can be subsequently characterized.

As indicated in step (4) of FIG. 4, the remaining sample which comprises numerous different isomer species each in different amounts, is then subjected to the scrambling conditions used in step 1. to regenerate scrambled isomers (i.e, a second round of scrambling). Under these conditions, equilibration among the denatured species results in the production of the desired isomer species, as took place in the first round of scrambling. The entire process of recycling of the equilibration of disulfide isomers may be repeated until a desired quantity of the desired isomer is obtained (i.e, numerous rounds of scrambling can be carried out).

The native protein used in the disulfide scrambling methods of the invention may be any protein containing at least two cysteine residues, and thus capable of forming at least one disulfide bond. Preferably the native protein comprises at least two disulfide bonds. The cysteines and disulfides of the protein may be naturally occurring in the protein's primary sequence (i.e., wild-type). In addition, the disulfide and cysteines of the protein may be genetically engineered (i.e, mutant). That is, at least one of the cysteines and/or resulting disulfides of the protein may be introduced into the protein by any modification method known by one of skill in the art useful for yielding the addition, deletion, replacement, shifting and/or modification of an amino acid in a protein sequence. The modification method may comprise non-chemical modification and/or chemical modification. The modification may also comprise rational design, or may be based on random mutation, or both. An example of a preferred technique well known to one of skill in the art is site-directed mutagenesis by use of PCR amplification.

Even another embodiment of the invention is directed to the conformational protein isomers produced by the methods of the invention. The isomers may be a single species of isomer, or may be a mixed population of isomers. The isomers may be purified or partially purified and all methods known to one of skill in the art for purifying proteins are applicable herein. Preferred purification methods include, for example, all forms of HPLC such as reversed-phase HPLC, size exclusion chromatography, and ion exchange chromatography. The isomers of the invention may be subjected to sequencing and any other additional analysis techniques, such as any physicochemical signal that distinguish the native and unfolded states such as spectra of fluorescence, circular dichroism, infrared, ultraviolet light and NMR coupled with amide proton exchange. Generally, the amino acid sequence of the isomers are analyzed by the well-known method of Edman degradation, for example, by use of a Perkin-Elmer Procise sequencer (Model 494) equipped with an on-line PTH-amino acid analyzer. Generally the molecular mass of the isomers is determined by MALDI-TOF mass spectrometry, another method well known to one of skill in the art. Because the disulfide scrambling method and isomer amplification method of the invention may be used on any native protein, the isomers of the invention may generally be isomers of any protein subjected to the present scrambling and amplification methods. Preferably the isomer is an isomer of cellular prion protein$^{PrPc}$, α-lactalbumin, epidermal growth factor, or potato carboxypeptidase inhibitor.

Preferred isomers of the invention include conformational isomers of α-lactalbumin. The conformational isomer may have any of the disulfide bond pairings/arrangements selected from those shown in the bottom portion of FIG. 5, wherein N is the native α-lactalbumin protein and a, b, c, d, e, and h are six isomers of α-lactalbumin, and wherein the disulfide bond pairings are as follows: for N, amino acid residues 6. and 120, 26. and 111, 61. and 77, and 73. and 91;. for a, amino acid residues 6. and 26, 61. and 73, 77. and 91, and 111. and 120;. for b, amino acid residues 6. and 26, 61. and 77, 73. and 91, and 111. and 120;. for c, amino acid residues 6. and 120, 26. and 111, 61. and 73, and 77. and 91;. for d, amino acid residues 6. and 26, 61. and 91, 73. and 77, and 111. and 120;. for e, amino acid residues 6. and 26, 61. and 120, 73. and 111, 77. and 91;. and for h, amino acid residues 6. and 26, 61. and 73, 77. and 111, and 91. and 120.

Other preferred isomers of the invention include conformational isomers of epidermal growth factor. The conformational isomer may have any of the disulfide bond pairings/arrangements selected from those shown in the top portion of FIG. 6, wherein A, B, C, D, E, F, G, and H are eight different isomers of EGF, and wherein the disulfide bond pairings are as follows: for A, amino acid residues 6. and 42, 14. and 33, and 20. and 31;. for B, amino acid residues 6. and 14, 20. and 31, and 33. and 42;. for C, amino acid residues 6. and 42, 14. and 31, and 20. and 33;. for D, 6. and 14, 20. and 33, and 31. and 42;. for E, 6. and 33, 14. and 20, and 31. and 42;. for F, 6. and 42, 14. and 20, and 31. and 33;. for G, 6. and 14, 20. and 42, and 31. and 33;. and for H, 6. and 31, 14. and 20, and 33. and 42.

Still another embodiment of the present invention is directed to therapeutic agents, and methods of making and using such agents. The process of drug discovery and development has, to date, largely been an undertaking of trial-and-error. However, it is clear that the greater the diversity of compounds screened and tested, the greater the chance that active compounds can be discovered and developed into drugs. The present invention provides this opportunity for greater diversity by providing the ability to produce and analyze large numbers of proteins in order to screen for new drugs and pharmaceutical compounds.

To utilize scrambled isomers as therapeutic agents, it is highly desirable that the isomers can be purified for structural analysis and functional evaluation. Scrambled isomers differ in their conformation and in subtle variation of hydrophobicity. While any technique for isolating and purifying proteins known by one of skill in the art may be used herein, preferably the technique of reversed phase HPLC is used for the separation of scrambled isomers.

A native protein and its numerous disulfide isomers all share the same amino acid sequence and identical molecular weight. They differ from each other only by their disulfide orientations and conformations. Some of these differences are subtle enough to enable the denatured isomers to act as either inhibitors or antagonists of the native protein. Regulation of disease-related proteins are major targets for drug discovery and generate demand for the design and synthesis of inhibitors and antagonists of the disease-associated protein. By using the technology of the present invention, it is possible to produce large numbers of conformational isomers. These isomers can then be studied in vitro and/or in vivo in order to determine the differences in biological function/activity between the different species of isomers and the native protein. This provides for the identification of isomers which function either as antagonists or agonists of the native protein useful as therapeutic agents in the treatment of conformational diseases associated with said native protein.

By combining an automated system for sample handling and rapid capillary electrophoresis for sample analysis, the technique of disulfide scrambling can be readily adapted to automation and high throughput screening of therapeutic agents. Any and all other techniques known in the art useful for automation of the present method for high throughput are applicable herein.

Yet another embodiment of the invention is directed to a protein library. Generally the protein library comprises at least two different species of isomer protein wherein the isomer proteins of each of the different species are conformational isomers of a native protein having a native conformation and native disulfide bonds. As the isomers are of the invention, the isomer proteins of each of the different isomer species have a species-specific non-native protein conformation comprising at least one non-native disulfide bond. Preferably, each of the different isomers species comprises at least two non-native disulfide bond. Each of the different species of isomer proteins of the library has its own unique non-native protein conformation, and each of the different species of isomer proteins differ from one another by at least one non-native disulfide bond. Preferably each of the species of isomer proteins differ from one another by the pairing of cysteine residues in at least two disulfide bonds.

Even still another embodiment of the present invention is directed to a method for screening the effectiveness of protein stabilizers. Protein stabilizers are small molecular weight compounds that protect and enhance the native conformation of proteins in solution. Some examples of known protein stabilizers include salts, glycerol, sugars, and amino acids. An insightful review dealing with the mechanism and function of protein stabilizers has been presented by Timasheff and colleagues (Timasheff, S. N. and Arakawa, T. (1990) Protein Structure, (ed. Creighton) IRL Press, pp.331-345), incorporated herein by reference.

Protein stabilizers are conventionally applied to preserve the stability and biological activity of proteins during their purification and long term storage. Their presence is known to shift the equilibrium constant of N (native)/D (denatured) in favor of the native structure. With the emerging number of cases of conformational diseases, compounds that act to stabilize proteins have become potential candidates for disease treatment and targets for drug discovery. Thus, protein stabilizers may also be useful as therapeutic agents/drug in the treatment of disease. With the technology of the present invention, it is possible to screen potential stabilizers and to analyze the effect of such stabilizers on vast numbers of conformational isomers.

Figure 7:
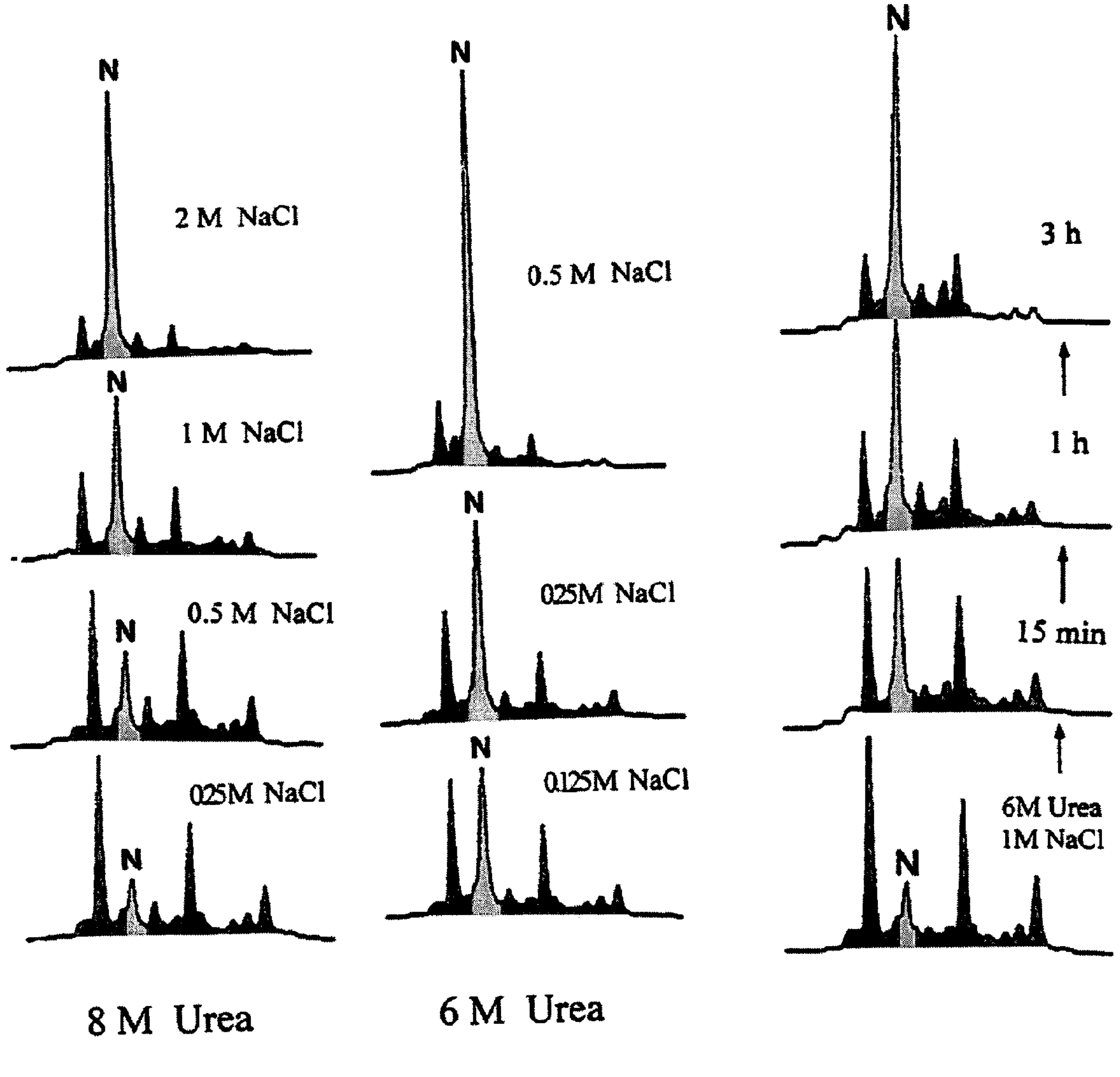
FIG. 7 provides HPLC analysis data of the reversible process of disulfide scrambling.

Results presented in FIG. 7 demonstrate that the presence of a protein stabilizer (NaCl in FIG. 7) can either inhibit the extent of protein denaturation(columns 1. and 2), or reverse the structure of a denatured protein (column 3). As shown in column (1) of FIG. 7, the extent of denaturation of tick anticoagulant peptide (TAP) by 8M urea was reduced by 23% and 50% in the presence of 0.5. M and 1M of NaCl respectively. As shown in column (3) of FIG. 7, the denatured TAP converts back to the native structure in the presence of urea after addition of the protein stabilizer.

The use of a protein stabilizer may be applied to any disulfide containing target protein for the evaluation of a wide range of protein stabilizers. Generally the method for assaying the effectiveness of an agent comprises a) contacting an effective amount of an agent together with a composition comprising at least one conformational isomer of the invention, and b) monitoring the ability of the agent to convert the conformation of the isomer into the conformation of the native protein.

By combining an automated system for sample handling and rapid capillary electrophoresis for sample analysis, the technique of disulfide scrambling can be readily adapted to automation and high throughput screening for protein stabilizers. Any and all other techniques known in the art useful for automation of the present method for high throughput are applicable herein.

Even yet another embodiment of the present invention is directed to methods for elucidating molecular mechanisms of conformational diseases. This method allows for (1) characterization of structures of misfolded (denatured) proteins and (2) elucidation of the pathway of conformational change of proteins that underlie conformational diseases. Conformational diseases are diseases caused by improper folding or conformational change of a protein. One major class of conformational diseases originates from the genetic variation that leads to amino acid replacement, misfolding, aggregation and malfunctioning of the encoded protein. Numerous diseases such as, for example, $a_1$-antitrypsin deficiency and cystic fibrosis are associated with such genetic defects. A Z-type mutation of $a_1$-antitrypsin, which causes aggregation of the molecule and deficiency of the functional protein is often linked to emphysema. Cystic fibrosis is a consequence of mutation of the gene encoding cystic fibrosis transmembrane conductance regulator (CFTR) which results in incorrect folding and hence diminished secretion of CFTR for required function.

A second important category of conformational disease is associated mainly with a group of neuro-degenerative disorders, which include mad cow disease, scrapie in sheep, Creutzfeldt-Jacob disease and familial insomnia in human etc., as well as the prevalent Alzheimer disease. These diseases are triggered by the conformational change of relevant proteins or protein fragments from their soluble form to the insoluble structures. The insoluble isomer subsequently aggregates to form fibrils or plaques which are major pathological hallmarks of many neuro-degenerative diseases. Among them, the prion disease represents the most fascinating and challenging subject.

A method of the invention useful for identifying a protein associated with disease generally comprises the steps of a) assaying the ability of a protein to promote disease in a cellular system, wherein said protein is an isomer protein of the invention. Generally the disease is a protein conformation-associated disease. The disorder may be in any stage of progression or development. The protein conformation-associated disorder may be any protein conformation-associated disorder such as, for example, any prion-associated disease, mad cow disease, scrapie in sheep, Creutzfeldt-Jacob disease and familial insomnia in human, Alzheimer disease, $a_1$-antitrypsin deficiency and cystic fibrosis.

Figure 8:
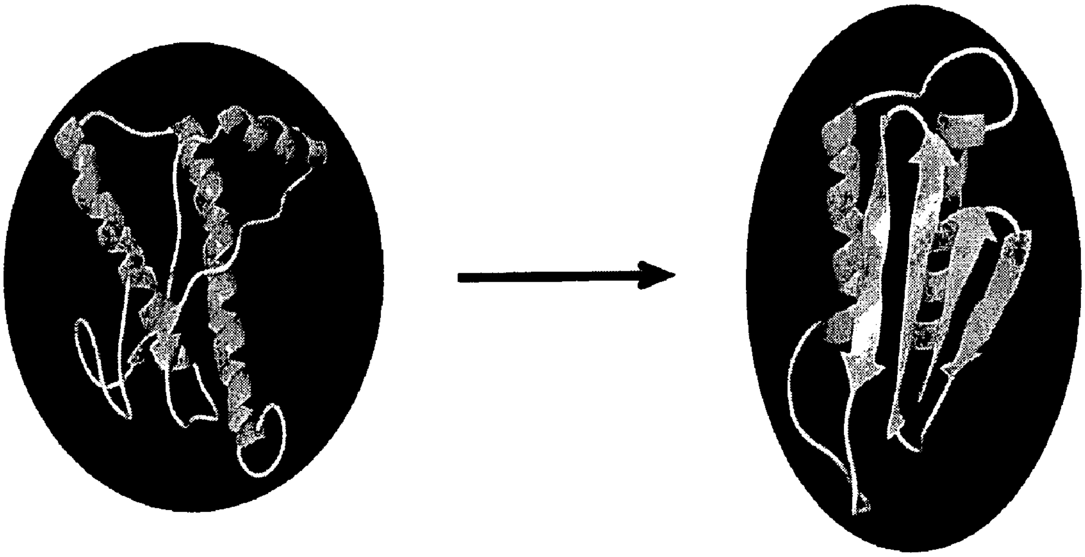
FIG. 8 provides a comparison between the mouse cellular prion and the proposed structure of infectious scrapie prion.

An example of a conformational disease suitable for such analysis is prion disease which is a disease that has been linked to numerous neurological disorders, most notably the recent outbreak of the mad cow disease in Great Britain, and a new strain of Creutzfeldt-Jacob disease that is transmitted to human through beef consumption. The prion disease is caused by conformational change of the benign cellular prion ($PrP^C$) into the infectious scrapie prion ($PrP^{SC}$) (FIG. 8). This structural change is characterized by a decrease of α-helical structure, an increase of β-sheet content and the formation of $PrP^{SC}$. amyloid. The molecular basis of this conformational change is central to understanding prion disease.

Two important aspects of prion disease remain to be elucidated: (1) the detailed structure of the scrapie prion ($PrP^{SC}$) and its strain-related isoforms; and (2) the molecular mechanism for the conversion of the cellular prion ($PrP^C$) to the scrapie prion ($PrP^{SC}$). Answers to these two important issues may be provided by the present technique of disulfide scrambling. The prion molecule contains one disulfide bond between cysteine 179. (Cys179) and cysteine 214. (Cys214). It is possible to introduce at least one additional disulfide bond through site-directed mutagenesis without altering the overall conformation of the prion molecule, producing a mutant which may be a useful compound for diagnosing the prion disease.

Figure 9:
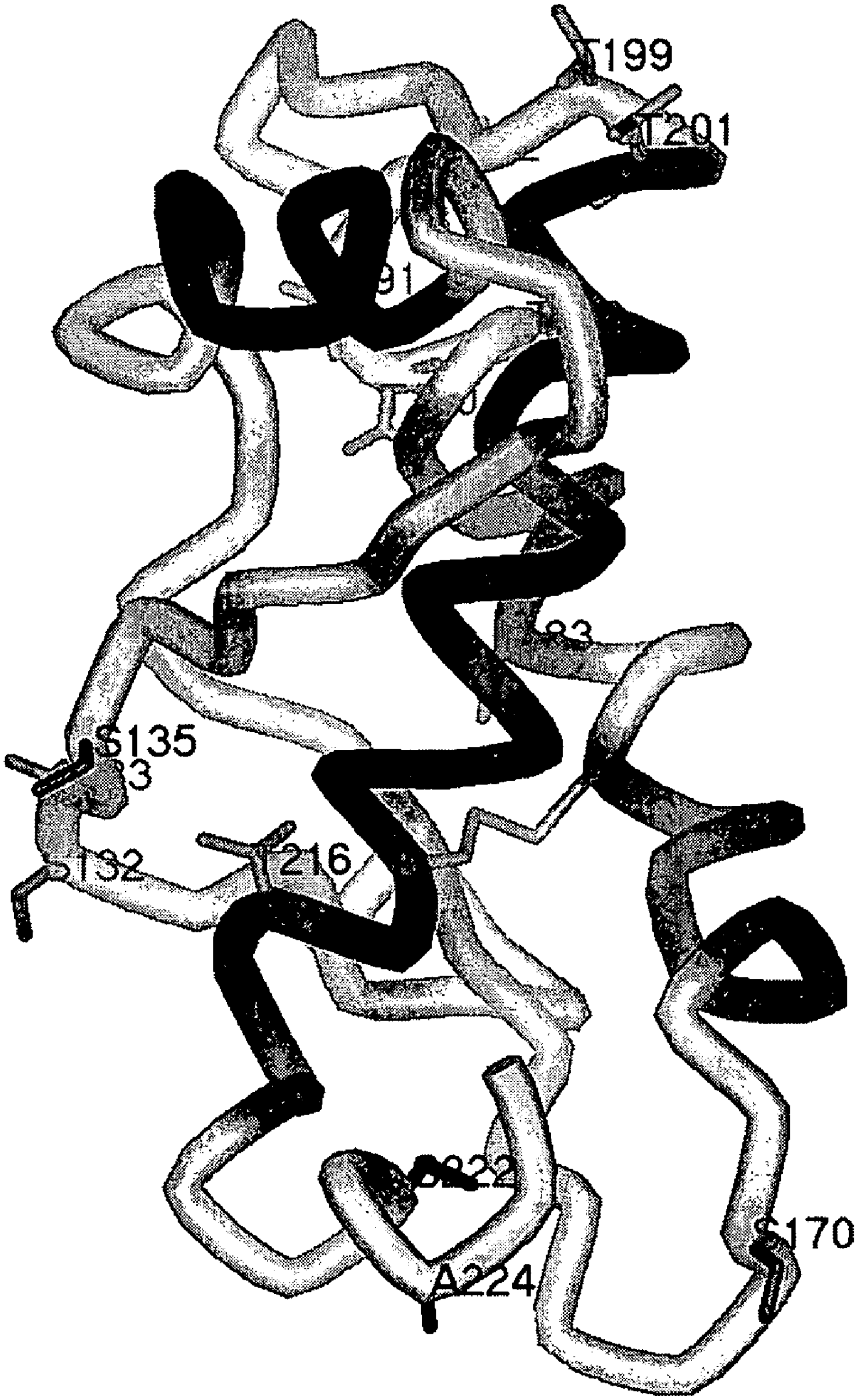
FIG. 9 illustrates the potential sites of mouse prion for amino acid replacement by cysteine residues.
Figure 10:
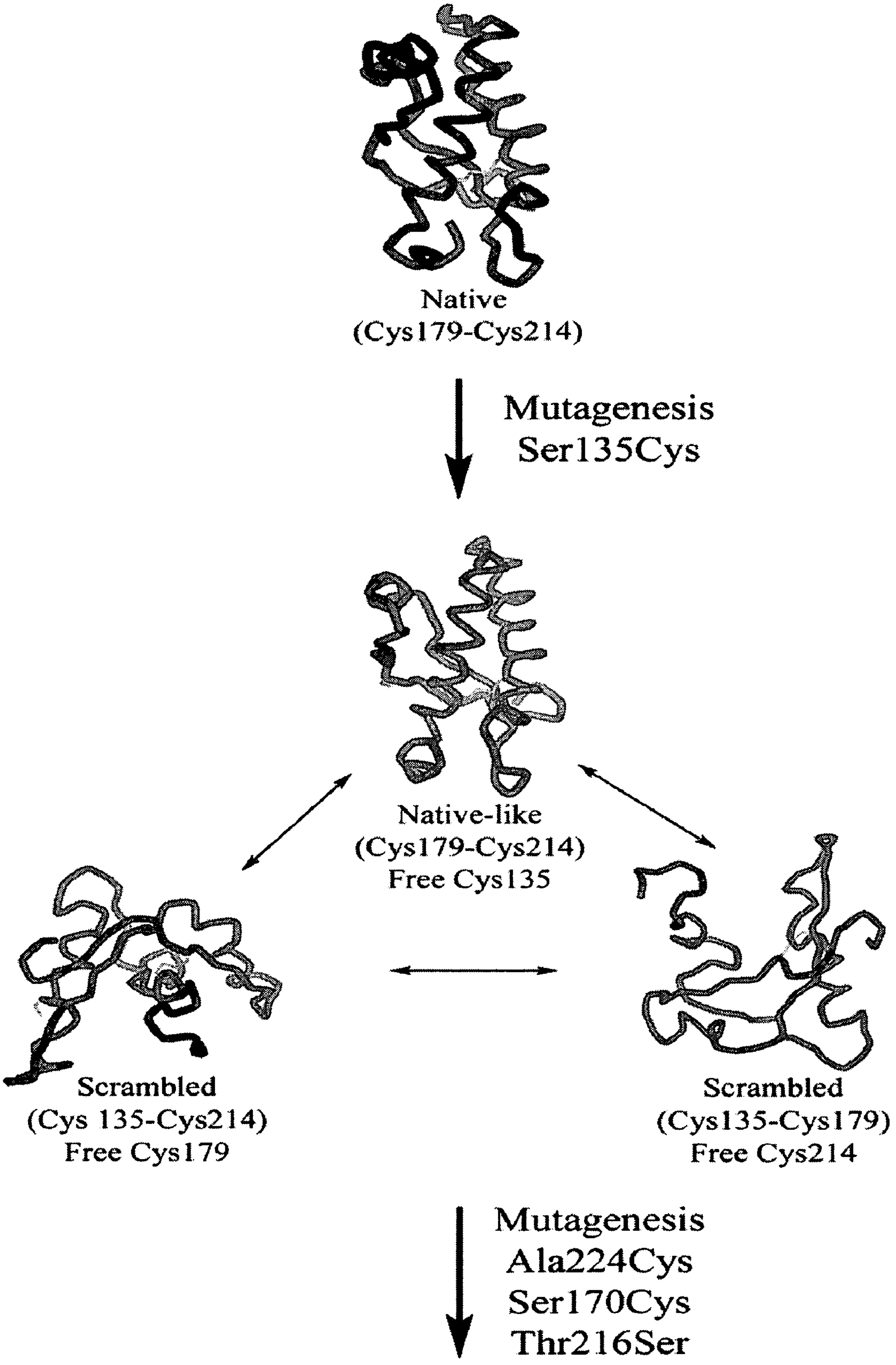
FIG. 10 schematically illustrates three different conformations of denatured prion resulting from a single amino acid residue replacement by a cysteine residue.

The process of diagnosis is achieved by incubating the prion mutant in an in vivo or in vitro cellular system that promotes the growth of the disease. The development of the disease is consequently monitored by trapping, isolating and analyzing the structure of the prion mutant. If required, a labeled prion mutant may be utilized to facilitate isolation and characterization. Any technique known in the art to be useful for the characterization of proteins may be used herein. Examination of the 3D structure of the mouse prion suggests at least two potential sites for the insertion of disulfide linkages that would trigger a minimum disturbance on its conformation. Those sites include Ser135, Thr216, Ser170, and Ala224. (FIG. 9). Even the introduction of a single cysteine may be sufficient to produce mutant prion proteins useful for in analysis by the technique of disulfide scrambling (FIG. 10).

Still even another embodiment of the present invention is directed to compositions. The compositions of the invention generally comprise at least one disulfide containing conformational isomer of a protein of interest. The compositions of the invention are useful in screening potency of an agent such as, for example, a drug or a protein stabilizer. The compositions of the present invention are also useful in treating a patient having a protein conformation disorder. The compositions of the present invention comprising scrambled isomers are also useful in vaccines.

The preparation of compositions is well known in the art, and all such techniques are appropriate in preparing the compositions of the present invention, and are incorporated herein by reference. The compositions of the present invention may further comprise a pharmaceutically acceptable carrier/vehicle. Pharmaceutically acceptable carriers/vehicles are known in the art and include aqueous solutions, non-toxic excipients, including salts, preservatives, buffers and the like, propylene glycol, polyethylene glycol, vegetable oil, injectable organic esters such as ethyloleate, water, saline solutions, parenteral vehicles such as sodium chloride and Ringer's dextrose, glycerol, lipids, and alcohols.

Compositions of the present invention may be manufactured into any form known in the art such as an orally digestible form, a sterile injectable form, forms suitable for delayed release, and forms that are enterically coated. Compositions of the invention may be in solid forms, including, for example, powders, tablets, pills, granules, capsules, sachets and suppositories, or may be in liquid forms including solutions, suspensions, gels and emulsions.

It may be desirable to express the proteins of the present invention from expression vectors. Vectors utilized herein may be any expression vector known in the art. Suitable expression vectors known in the art include bacterial vectors, viral vectors, and eukaryotic vectors such as, for example, yeast vectors and mammalian vectors. In principle, all vectors which replicate and express the desired sequence according to the invention in the chosen host are suitable. Thus, the vector may be a plasmid or the vector may be a viral vector such as, for example, a retroviral vector, an adeno associated vector, an adenoviral vector, or a herpes viral vector.

Still yet another embodiment of the present invention is directed to methods for treating a patient afflicted with a disorder comprising altered protein conformation. Generally the treatment method of the invention comprises a) administering an effective dose of a composition of the invention to a patient.

One method of the invention for treating a patient comprises the step of a) administering an effective dose of a composition to a patient afflicted with a disease associated with an isomer protein having at least one disulfide bond. Preferably the isomer has at least two disulfide bonds. The disease-associated isomer protein is a conformational isomer of a native protein having a native conformation and native disulfide bonds, and the at least one disulfide bond of the disease-associated isomer is a non-native disulfide bond. The composition comprises an effective dose of at least one agent which causes the non-native conformation of said isomer protein to convert into the native conformation of the native protein. Generally the disorder is selected from the group consisting of prion-associated diseases, mad cow disease, scrapie in sheep, Creutzfeldt-Jacob disease, familial insomnia, Alzheimer disease, $a_1$-antitrypsin deficiency and cystic fibrosis. In a preferred embodiment the agent is a protein stabilizer. The effectiveness of the protein stabilizer may be assayed by the screening methods of the invention.

Another method of the invention for treating a patient comprises the step of: a) administering an effective dose of a composition to a patient afflicted with a disease associated with an isomer protein having at least one disulfide bond. Preferably the disease-associated isomer has at least two disulfide bonds. The disease-associated isomer protein is a conformational isomer of a native protein having a native conformation and native disulfide bonds, and the at least one disulfide bond of the disease-associated isomer is a non-native disulfide bond. The composition comprises an effective dose of a compound which has activity as an antagonist to the disease-associated isomer. In a preferred embodiment the agent is an antagonistic isomer protein having at least one disulfide bond, wherein the antagonistic isomer protein is a conformational isomer of the same native protein, and wherein the antagonistic isomer protein and disease-associated isomer protein differ from one another by protein conformation and by at least one disulfide bond. Generally the antagonistic agent is identified by the screening methods of the invention.

As used herein, the word "patient" includes any and all organisms capable of developing a disorder wherein the disorder is associated with conformational change of a disulfide-containing protein. Preferably, the patient of the invention is a mammal. In a particularly preferred embodiment, the patient is a human.

One preferred treatment method of the present invention takes advantage of the reversible conversion between the active, native structure and an inactive, scrambled structures as an off-on switch for drug delivery and release. Generally, an inactive, scrambled form of a protein drug is first delivered to a target tissue, organ, or locale within the body of the patient. An effective dose of thiol catalyst is then administered to the target tissue, organ, or locale within the body of the patient. The addition of the thiol catalyst serves to cause the inactive isomer to regenerate/reproduce the activate, native protein structure. By administering different doses of isomer, and also of thiol catalyst, the rate of regeneration/release of the native active protein can be controlled. Thus, the process can be tailored to be a time-release based therapy.

The compositions and methods of the invention are useful for treating a patient afflicted with any protein conformation-associated disorder/disease. The disorder may be in any stage of progression or development. The protein conformation-associated disorder may be any protein conformation-associated disorder such as, for example, any prion-associated disease, mad cow disease, scrapie in sheep, Creutzfeldt-Jacob disease and familial insomnia in human, Alzheimer disease, $a_1$-antitrypsin deficiency and cystic fibrosis.

The administration of the compositions of the present invention may be by any method known in the art. Thus, administration of the present invention to a recipient/patient may be by a route selected from oral, parenteral (including, subcutaneous, intradermal, intramuscular, and intravenous) and rectal. For increased efficacy, the compositions of the present invention may be administered via localized delivery to a targeted region or tissue. Preferably the compositions of the present invention are administered orally or parenterally, specifically intravenously.

The compositions and treatment methods of the present invention may be administered to and performed upon a recipient/patient as a single dose unit, or may be administered in several dose units, for a period ranging from one day to several years. The dose schedule is dependent upon at least the severity of the patient's disorder, as well as the composition and mode of administration. The effective dose of the present invention may further depend upon the body weight (BW) of the patient.

All references cited in the present application, including journal articles, laboratory manuals, all U.S. and foreign patents and patent applications, are specifically and entirely incorporated by reference.

EXAMPLES

The following examples are provided to illustrate the present invention. These examples are not intended to limit the scope of the claims of the present invention, and should not be so interpreted.

Example 1

Preparation of Conformational Isomers of α-Lactalbumin

Native protein (0.5. mg/ml) was dissolved in Tris-HCl buffer (0.1. M), pH 8.4) containing 0.02-0.25. mM of 2-mercaptoethanol and various selected condition of a denaturant (GdmCl—1.25M, 1.75M, 3M, 5M, and 8M, with and without 5. mM $CaCl_2$; GdmSCN—0.5M, 0.75M, 1.5M, 3M, and 6M; urea—2M, 4M, 4.5M, 6M, and 8M, with and without 5. mM $CaCl_2$; acetonitrile ($CH_3CN$)—40% acetonitrile for 2. hours, 4. hours and 24. hours, with and without 5. mM $CaCl_{2)}$) as indicated in FIG. 11 top and bottom. The reaction was allowed to reach equilibrium and was typically performed at 23° C. for 24-48. hours. For thermal denaturation, the sample was in the presence of 0.1. mM 2-mercaptoethanol and subjected to elevated temperature (45-65° C.) for a time period of up to 60. minutes. To monitor the kinetics of denaturation and unfolding, aliquots of the sample are removed at time intervals, quenched with 4% trifluoroacetic acid and analyzed by HPLC. The denatured and acidified sample is subsequently stored at a temperature of less than 0° C., preferably at about −20° C. For large scale production, denaturant and thiol agent are removed by gel filtration (e.g. PD-10. or NAP-5. columns from Pharmacia AG), eluted with 1% trifluoroacetic acid. Denatured scrambled isomers are totally stable at −20° C. for at least 8. years.

The top portion of FIG. 11 illustrates the thermodynamic denaturation of α-lactalbumin by the different concentrations of urea (2, 4, 4.5, 6, and 8M), GdmCl (1.25, 1.75, 3, 5, and 8M), and GdmSCN (0.5, 0.75, 1.5, 3, and 6M). The native protein is depicted by N and the isomers are depicted by a, b, c, d, e, f, and h.

The bottom portion of FIG. 11 provides thermodynamic denaturation curves of α-lactalbumin. These curves were derived form data presented in the top portion of FIG. 11. "Fractions denatured" indicates the fraction (%) of native α-lactalbumin converted to scrambled α-lactalbumin.

Example 2

Different Denaturing Conditions to Produce Different Isomers of α-Lactalbumin.

Figure 5:
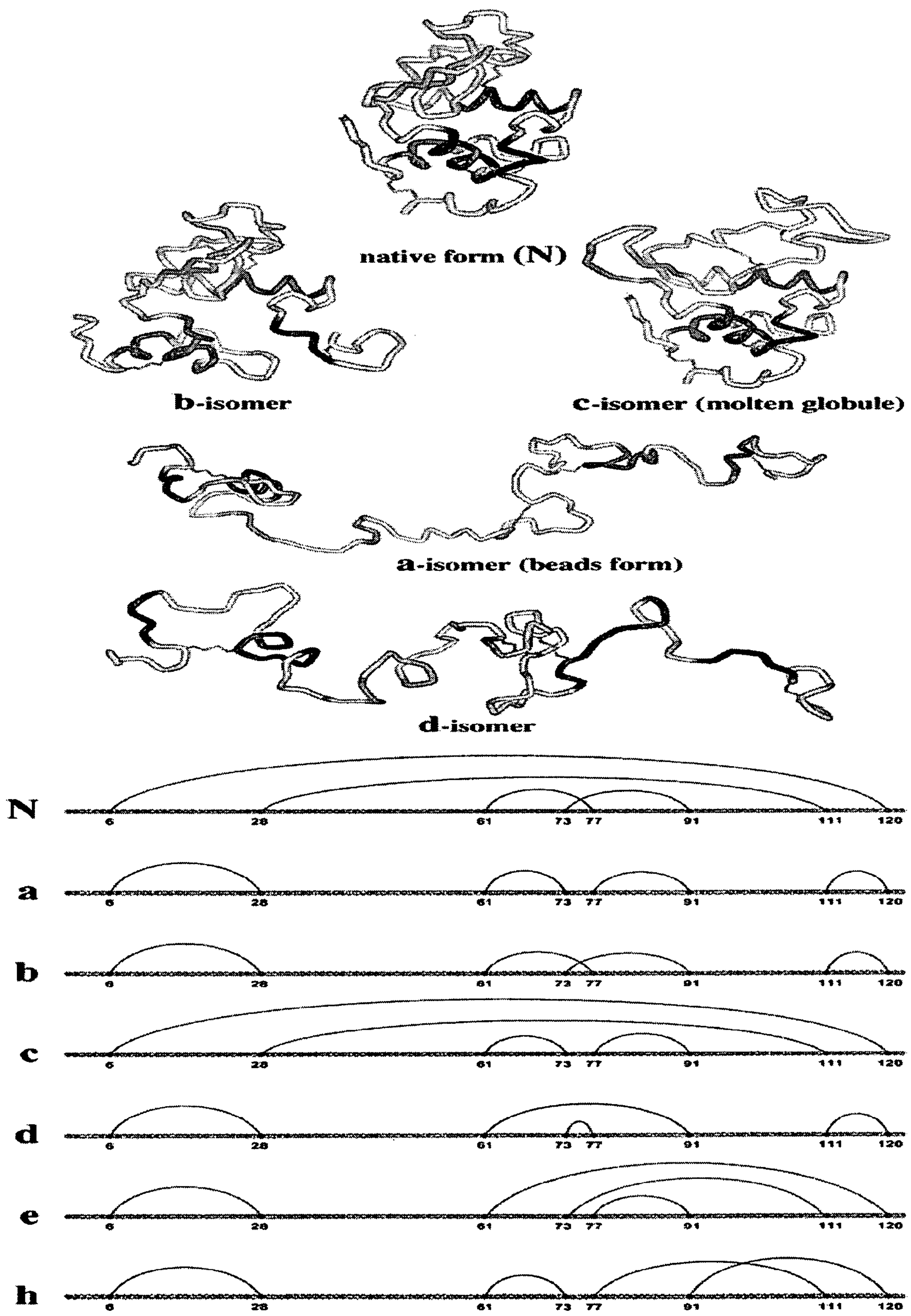
FIG. 5 schematically illustrates the conformation of native α-lactalbumin (N) and 4. denatured conformational isomers of α-lactalbumin (a-d) (Top portion), and the disulfide pairings of native α-lactalbumin (N) and 6. denatured conformational isomers of α-lactalbumin (a-e and h) (Bottom portion).
Figure 12:
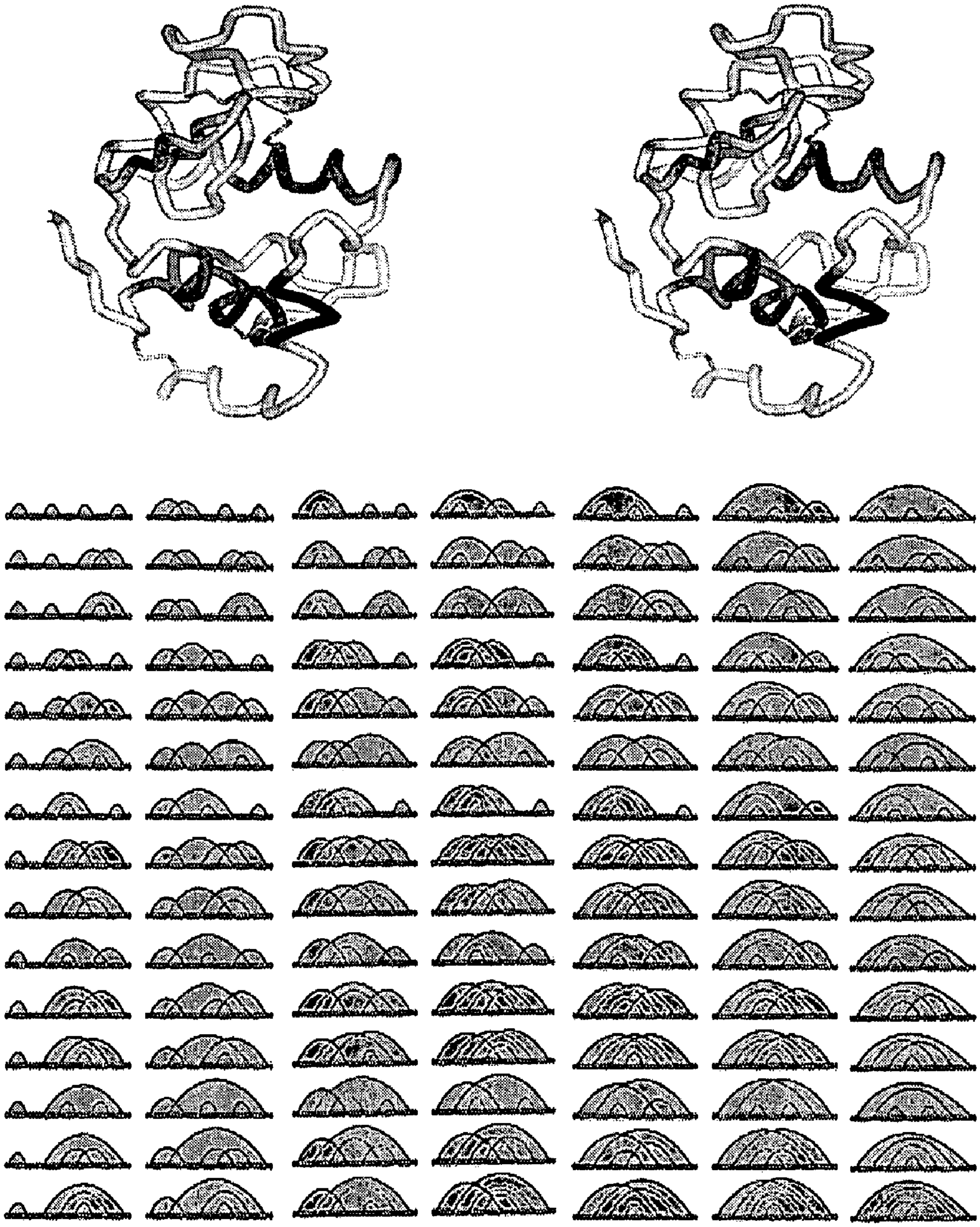
FIG. 12 schematically illustrates 104. different α-lactalbumin disulfide isomers.

The populations of scrambled isomers produced by the present method is determined at least by the denaturing conditions. α-lactalbumin, the regulatory subunit of lactose synthetase, is one of the most extensively investigated models for understanding protein stability, folding and unfolding. α-lactalbumin contains 122. amino acids, four disulfide bonds and can potentially form 104. scrambled isomers (FIG. 12). Using the technique of disulfide scrambling of the present invention, denatured α-lactalbumin was found to consist of at least 50. fractions of scrambled isomers. Among these, the disulfide structures/pairings of six major scrambled isomers (FIG. 5 top, a, b, c, d, e, and h) have been determined (FIG. 5, bottom). Two of them, a and d, are extensively denatured species, and two others, b and c, are partially denatured species comprising partly structured and partly unstructured domains.

Choosing different specific denaturing conditions may be necessary for production of favored isomers. For example, to produce high concentration of isomer c, thermal denaturation at a temperature of about 65° C. may be utilized, shown in FIG. 13(A). To generate high concentration of isomer b, organic solvent such as 30-40% acetonitrile may be utilized as the denaturant shown in FIG. 13(B). To generate the isomers of α-lactalbumin with a maximized heterogeneity, a concentration of about 1.25M GdmCl, shown in FIG. 13(C), or about 0.75. M GdmSCN, as shown in FIG. 13(D), may be used as the denaturant. To produce high concentrations of isomers a and d, high concentration of GdmCl (about 8. M) (FIG. 13(E)), or GdmSCN (6. M) (FIG. 13(F)) may be used as the denaturant. The art of generating selective populations of disulfide isomers by the above mentioned technique is a novel process.

Figure 14:
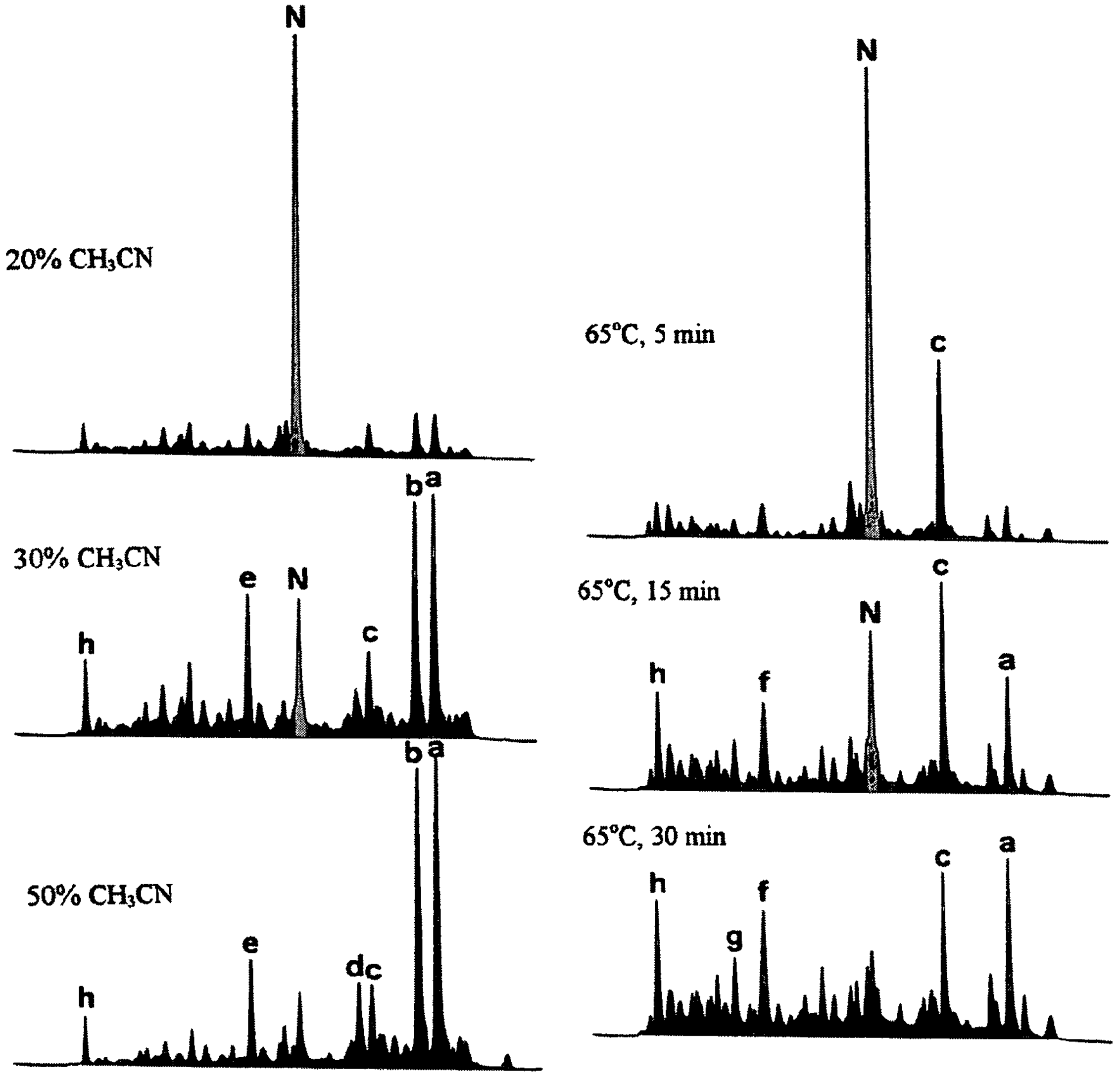
FIG. 14 provides HPLC analysis data for native α-lactalbumin (N) and various denatured α-lactalbumin isomers (a-h).

The denaturation of α-lactalbumin to generate scrambled isomers was also carried out using elevated temperature and also by using organic solvent (acetonitrile) (FIG. 14). Time-course thermal denaturation of α-lactalbumin reveals the presence of a major unfolded intermediate (isomer c, see right panel of FIG. 14) with a largely intact α-helical domain and an unstructured, disordered α-sheet region (for the structure of isomer c, see top portion of FIG. 5). This allows identification of unfolding intermediates and elucidation of an unfolding pathway through analysis of a set of denatured structures. These results also quantitatively display that a denatured protein can adopt a large variety of structures. In the case of α-lactalbumin, each denaturing condition generates a unique structure of denatured α-lactalbumin, as shown by the diverse composition of scrambled isomers (see FIGS. 13 and 14).

Example 3

Generation of Conformational Isomers of EGF.

Figure 6:
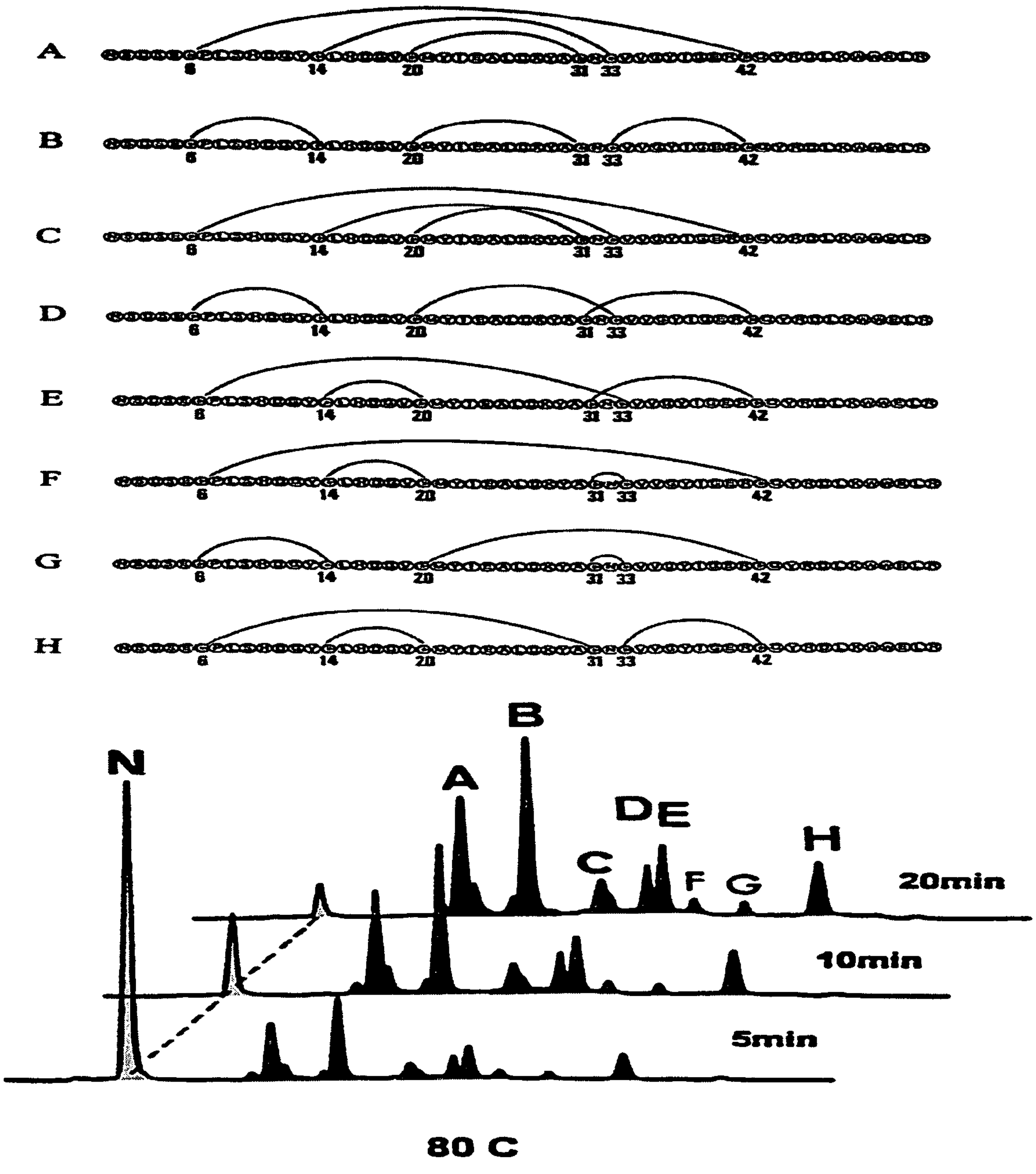
FIG. 6 illustrates disulfide bond pairings of eight isomers of scrambled EGF (A-H) (Top portion), and the HPLC profiles of 8. different conformational isomers (A-H) of EGF generated at high temperature (Bottom portion).

Human epidermal growth factor (EGF) is a 3-disulfide-containing, 6. kd polypeptide that stimulates the growth of epidermal and epithelial cells by binding to the EGF receptor. Conformational isomers of EGF were generated via thermal denaturation of the native species (N) (FIG. 6). Eight fractions of scrambled isomers (A, B, C, D, E, F, G, and H) of denatured EGF were purified and structurally characterized. Each of them is shown to contain a pure species of disulfide isomer, shown in bottom portion of FIG. 6. As known by one of skill in the art, their structures were determined by analysis of thermolytic peptides using Edman sequencing and MALDI mass spectrometry.

Example 4

Display of Biological Function by Scrambled Potato Carboxypeptidase Inhibitor Isomers.

Figure 15:
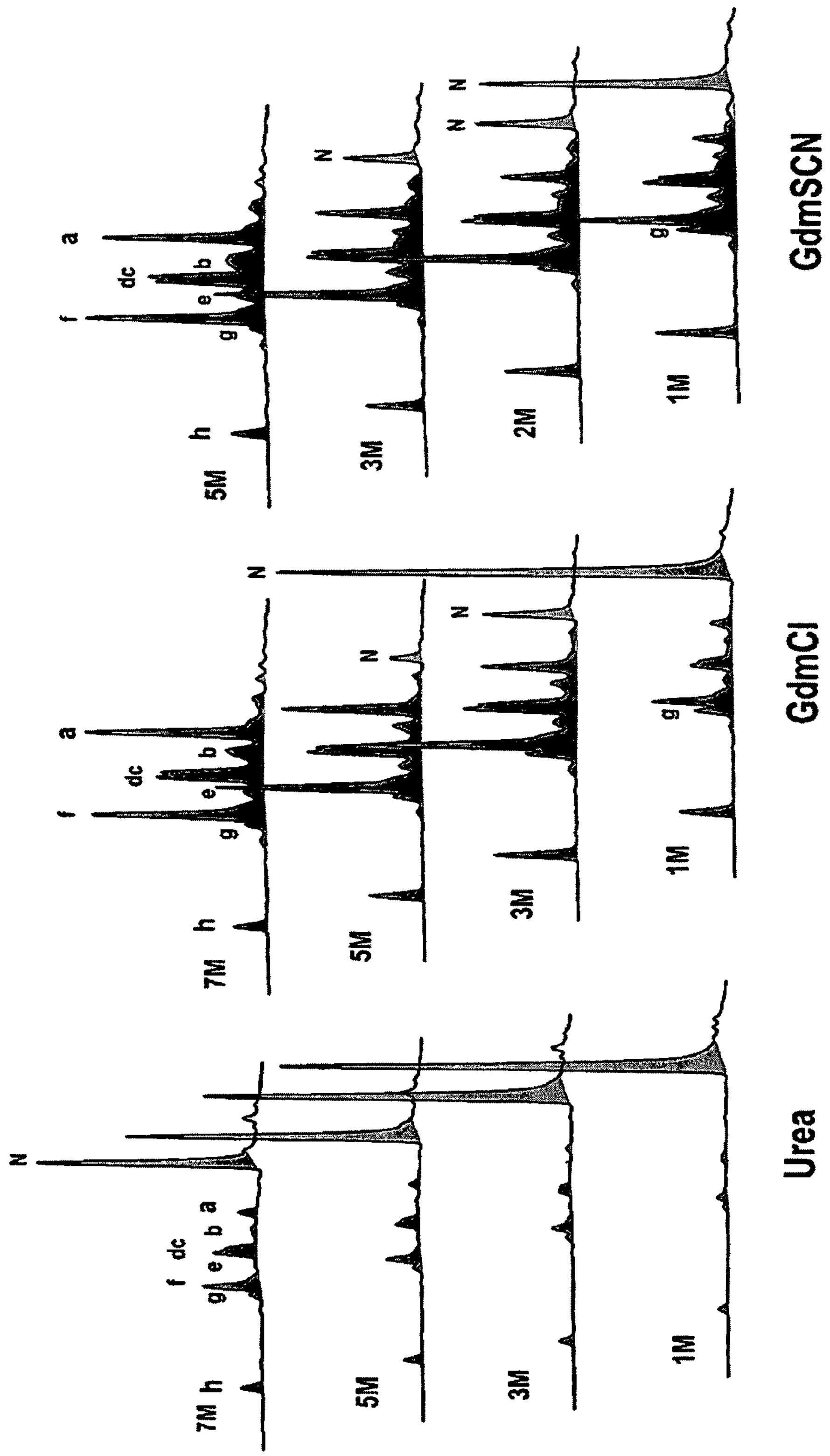
FIG. 15 provides HPLC analysis of denature states of PCI under different denaturing conditions.

Potato carboxypeptidase inhibitor (PCI) contains three disulfides and is an inhibitor of insect digestive metallo-carboxypeptidase. PCI functions as part of the defense mechanism of the potato plant against insect attack, and has also been recently shown to possess anti-tumoral activity. Native PCI was scrambled using the following denaturant as described in FIG. 15: Urea at 1M, 3M, 5M, and 7M; GdmCl at 1M, 3M, 5M, and 7M; and GdmSCN at 1M, 2M, 3M, and 5M. Denatured PCI comprises 8. fractions of scrambled isomers, shown in FIG. 15 (N=native PCI; a, b, c, d, e, f, g, and h=scrambled PCI isomers). Four of them, d, f, g and h, exhibit biological activity. That is, isomers d, f, g, and h inhibit carboxypeptidase with a binding affinity (ki) of $2.6\times10^{-6}$M (species d), $10\times10^{-6}$M (species f), $4.8\times10^{-6}$M (species g) and $7.0\times10^{-6}$M (species h), respectively. These binding affinities are highly significant and though the mode of their binding to carboxypeptidase may vary, the overall end result is binding with carboxypeptidase of about 1000. fold weaker than that of native PCI.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein, but rather that the claims be construed as encompassing all the features of patentable novelty which reside in the present invention, including all features which would be treated as equivalents thereof by those skilled in the art to which this invention pertains.

I claim:

1. A method for producing stable isomers of a protein, the method comprising:

denaturing a sample comprising a recombinantly modified protein comprising at least one non-native cysteine in a denaturing buffer under incubation conditions sufficient to produce a mixture of stable isomer proteins, wherein said stable isomer proteins have a non- native conformation and comprise at least one non-native disulfide bond, isolating said stable isomer proteins, and screening the stable isomer proteins for use as a therapeutic agent, wherein the protein is not hirudin, tick anticoagulant peptide, potato carboxypeptidase inhibitor, or α-lactalbumin.

2. The method of claim 1 wherein said buffer comprises a denaturant.

3. The method of claim 2 wherein said denaturant is selected from the group consisting of urea, guanidinium chloride (GdmCl), guanidine thiocyanate (GdmSCN), organic solvents, elevated temperature, extreme pH, surfactants and detergents, and mechanical forces such as shaking, shearing, ultrasound, radiation and pressure.

4. The method of claim 1 wherein said buffer comprises a thiol agent.

5. The method of claim 4 wherein said thiol agent is selected from the group consisting of 2-mercaptoethanol, reduced glutathione, cysteine, and thiol-containing chemical compounds.

6. The method of claim 1 wherein said incubation conditions comprise a temperature of between about 23° C. to about 37° C., and a time period ranging from about 15 minutes to about 7 days.

7. The method of claim 1 wherein said recombinantly modified proteins comprises at least two non-native disulfide bonds.

8. The method of claim 1 wherein said mixture comprises more than one species of stable isomer proteins, wherein each of the more than one species of stable isomer proteins has a species-specific non-native conformation, and wherein each of the more than one species of stable isomer proteins differs from one another by its species-specific non-native conformation.

9. A method for selectively making stable non-native protein isomers, the method comprising: denaturing a modified protein comprising at least one new disulfide bonding site in a denaturing buffer under incubation conditions sufficient to produce a mixture of stable modified protein isomers; isolating one or more of the stable modified protein isomers; and screening the isolated stable modified protein isomers for use as a therapeutic agent, wherein the protein is not hirudin, tick anticoagulant peptide, potato carboxypeptidase inhibitor, or α-lactalbumin.

10. The method of claim 9, wherein the buffer comprises a denaturant selected from the group consisting of urea, GdmCl, GdmSCN and organic solvents.

11. The method of claim 9, wherein the conditions comprise denaturing conditions selected from the group consisting of elevated temperature, extreme pH, surfactants and detergents, and mechanical forces such as shaking, shearing, ultrasound, radiation and pressure.

12. The method of claim 9, wherein the buffer comprises a thiol agent selected from the group consisting of 2-mercaptoethanol, reduced glutathione and cysteine.

13. The method of claim 9, wherein the incubation conditions comprise a temperature of between about 23° C. to about 37° C.

14. The method of claim 9, wherein the incubation conditions comprise a time period ranging from about 15 minutes to about 7 days.

15. The method of claim 1, wherein the mixture of stable isomer proteins comprises a desired stable isomer population, wherein the desired stable isomer population is produced by choosing specific incubation conditions.

16. The method of claim 1, wherein the mixture of stable isomer proteins comprises an agonist of the native protein.

17. The method of claim 1, wherein the mixture of stable isomer proteins comprises an antagonist of the native protein.

18. The method of claim 1, wherein specific incubation conditions are chosen, wherein the specific incubation conditions chosen produce a specific population of stable isomer proteins.

19. The method of claim 9, wherein specific incubation conditions are chosen, wherein the specific incubation conditions chosen produce a specific population of stable modified protein isomers.

20. The method of claim 1, wherein the stable isomer proteins are screened for use as a therapeutic agent for treatment of a conformational disease.

21. The method of claim 1 further comprising treating a conformational disease with one or more of the stable isomer proteins identified as useful as a therapeutic agent.

22. The method of claim 9, wherein the stable modified protein isomers are screened for use as a therapeutic agent for treatment of a conformational disease.

23. The method of claim 9 further comprising treating a conformational disease with one or more of the stable isomer proteins identified as useful as a therapeutic agent.

24. The method of claim 5, wherein said thiol agent is selected from, the group consisting of 2-mercaptoethanol, reduced glutathione, and cysteine.

25. A method for producing stable isomers of a protein, the method comprising:

denaturing a sample comprising a starting protein in a denaturing buffer under incubation conditions sufficient to produce a mixture of stable isomer proteins, wherein the denaturing buffer comprises a thiol agent, wherein the incubation conditions leave the protein fully oxidized, wherein the stable isomer proteins have a non-native conformation, comprise at least one non-native disulfide bond that was not present in the starting protein, isolating the stable isomer proteins, and screening the stable isomer proteins for use as a therapeutic agent, wherein the protein is not hirudin, tick anticoagulant peptide, potato carboxypeptidase inhibitor, or α-lactalbumin.

26. The method of claim 25, wherein the starting protein is a native protein having only native disulfide bonds.

27. The method of claim 25, wherein the protein comprises at least one non-native cysteine.

28. The method of claim 25, wherein the protein has at least one native cysteine replaced.

29. The method of claim 25, wherein a stable isomer protein is identified as a therapeutic agent.

30. The method of claim 1, wherein a stable isomer protein is identified as a therapeutic agent.

31. The method of claim 9, wherein a stable modified protein isomer is identified as a therapeutic agent.

32. A method for producing stable isomers of a protein, the method comprising:

denaturing a sample comprising a recombinantly modified protein comprising at least one non-native cysteine in a denaturing buffer under incubation conditions sufficient to produce a mixture of stable isomer proteins, wherein said stable isomer proteins have a non- native conformation and comprise at least one non-native disulfide bond, wherein the incubation conditions leave the protein fully oxidized, isolating the stable isomer proteins, and screening the stable isomer proteins for use as a therapeutic agent, wherein the protein is not hirudin, tick anticoagulant peptide, potato carboxypeptidase inhibitor, or α-lactalbumin.

33. The method of claim 1, wherein the protein remains fully oxidized under the incubation conditions.

34. The method of claim 9, wherein the protein remains fully oxidized under the incubation conditions.

* * * * *

UNITED STATES PATENT AND TRADEMARK OFFICE

CERTIFICATE OF CORRECTION

PATENT NO. : 7,601,683 B2
APPLICATION NO. : 10/210862
DATED : October 13, 2009
INVENTOR(S) : Rowen J. Y. Chang It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 335 days.

Signed and Sealed this

Fifth Day of October, 2010

David J. Kappos
*Director of the United States Patent and Trademark Office*